United States Patent [19]
Harrison et al.

[11] Patent Number: 5,849,297
[45] Date of Patent: Dec. 15, 1998

[54] MODIFIED HUMAN C3 PROTEINS

[75] Inventors: Richard Alexander Harrison; Timothy Charles Farries, both of Cambridge, Great Britain

[73] Assignee: Imutran Limited, Great Britain

[21] Appl. No.: 793,126

[22] Filed: Feb. 7, 1997

Related U.S. Application Data

[63] Continuation of PCT/GB95/02121, Sep. 8, 1995.

[30] Foreign Application Priority Data

Sep. 8, 1994 [GB] United Kingdom ............... 9418147
May 4, 1995 [GB] United Kingdom ............... 9509102

[51] Int. Cl.⁶ .................. C07K 16/46; C07K 14/745; A61K 38/36; A61K 39/395
[52] U.S. Cl. .............. 424/178.1; 530/381; 530/402; 530/391.7; 435/226; 514/12; 424/94.64
[58] Field of Search .................... 530/381, 402, 530/391.7; 435/226; 514/12; 424/94.64, 178.1

[56] References Cited

U.S. PATENT DOCUMENTS 4,661,347  4/1987  Muller-Eberhard et al. ............. 424/85

OTHER PUBLICATIONS

R.R. Kew et al., "Cigarette Smoke Can Activate the Alternative Pathway of Complement In Vitro by Modifying the Third Component of Complement", J. Clin. Invest. 75: 1000–1007, Mar. 1985.

D.E. Isenman et al., "Nucleophilic Modification of Human Complement Protein C3: Correlation of Conformational Changes With Acquisition of C3b–like Functional Properties", Biochemistry 20: 4458–4467, Jul. 1981

Z. Fishelson et al., "Characterization of the Initial C3 Convertase of the Alternative Pathway of Human Complement", J. Immunol. 132 (3): 1430–1434, Mar. 1984.

*Primary Examiner*—Rebecca E. Prouty
*Attorney, Agent, or Firm*—Hale and Dorr LLP

[57] ABSTRACT

Narrative complement pathway proteins modified such that the protein is capable of forming a stable C3 convertase. Preferably the modified protein is a modified human C3 protein. DNA sequences encoding such proteins are also provided, together with DNA constructs. Conjugates comprising such proteins and a specific binding moiety, for example an antibody, are also described, as are uses of such proteins and/or conjugates in therapy.

15 Claims, 15 Drawing Sheets

```
       10         20         30         40         50         60
MGPTSGPSLL LLLLTHLPLA LGSPMYSIIT PNILRLESEE TMVLEAHDAQ GDVPVTVTVH 70         80         90        100        110        120
DFPGKKLVLS SEKTVLTPAT NHMGNVTFTI PANREFKSEK GRNKFVTVQA TFGTQVVEKV 130        140        150        160        170        180
VLVSLQSGYL FIQTDKTIYT PGSTVLYRIF TVNHKLLPVG RTVMVNIENP EGIPVKQDSL 190        200        210        220        230        240
SSQNQLGVLP LSWDIPELVN MGQWKIRAYY ENSPQQVFST EFEVKEYVLP SFEVIVEPTE 250        260        270        280        290        300
KFYYIYNEKG LEVTITARFL YGKKVEGTAF VIFGIQDGEQ RISLPESLKR IPIEDGSGEV 310        320        330        340        350        360
VLSRKVLLDG VQNPRAEDLV GKSLYVSATV ILHSGSDMVQ AERSGIPIVT SPYQIHFTKT 370        380        390        400        410        420
PKYFKPGMPF DLMVFVTNPD GSPAYRVPVA VQGEDTVQSL TQGDGVAKLS INTHPSQKPL 430        440        450        460        470        480
SITVRTKKQE LSEAEQATRT MQALPYSTVG NSNNYLHLSV LRTELRPGET LNVNFLLRMD 490        500        510        520        530        540
RAHEAKIRYY TYLIMNKGRL LKAGRQVREP GQDLVVLPLS ITTDFIPSFR LVAYYTLIGA 550        560        570        580        590        600
SGQREVVADS VWVDVKDSCV GSLVVKSGQS EDRQPVPGQQ MTLKIEGDHG ARVVLVAVDK 610        620        630        640        650        660
GVFVLNKKNK LTQSKIWDVV EKADIGCTPG SGKDYAGVFS DAGLTFTSSS GQQTAQRAEL 670        680        690        700        710        720
QCPQPAARRR RSVQLTEKRM DKVGKYPKEL RKCCEDGMRE NPMRFSCQRR TRFISLGEAC 730        740        750        760        770        780
KKVFLDCCNY ITELRRQHAR ASHLGLARSN LDEDIIAEEN IVSRSEFPES WLWNVEDLKE 790        800        810        820        830        840
PPKNGISTKL MNIFLKDSIT TWEILAVSMS DKKGICVADP FEVTVMQDFF IDLRLPYSVV 850        860        870        880        890        900
RNEQVEIRAV LYNYRQNQEL KVRVELLHNP AFCSLATTKR RHQQTITIPP KSSLSVPYVI 910        920        930        940        950        960
VPLKTGLQEV EVKAAVYHHF ISDGVRKSLK VVPEGIRMNK TVAVRTLDPE RLGREGVQKE
```

FIG.1A

```
         970        980        990       1000       1010       1020
    DIPPADLSDQ VPDTESETRI LLQGTPVAQM TEDAVDAERL KHLIVTPSGC GEQNMIGMTP 1030       1040       1050       1060       1070       1080
    TVIAVHYLDE TEQWEKFGLE KRQGALELIK KGYTQQLAFR QPSSAFAAFV KRAPSTWLTA 1090       1100       1110       1120       1130       1140
    YVVKVFSLAV NLIAIDSQVL CGAVKWLILE KQKPDGVFQE DAPVIHQEMI GGLRNNNEKD 1150       1160       1170       1180       1190       1200
    MALTAFVLIS LQEAKDICEE QVNSLPGSIT KAGDFLEANY MNLQRSYTVA IAGYALAQMG 1210       1220       1230       1240       1250       1260
    RLKGPLLNKF LTTAKDKNRW EDPGKQLYNV EATSYALLAL LQLKDFDFVP PVVRWLNEQR 1270       1280       1290       1300       1310       1320
    YYGGGYGSTQ ATFMVFQALA QYQKDAPDHQ ELNLDVSLQL PSRSSKITHR IHWESASLLR 1330       1340       1350       1360       1370       1380
    SEETKENEGF TVTAEGKGQG TLSVVTMYHA KAKDQLTCNK FDLKVTIKPA PETEKRPQDA 1390       1400       1410       1420       1430       1440
    KNTMILEICT RYRGDQDATM SILDISMMTG FAPDTDDLKQ LANGVDRYIS KYELDKAFSD 1450       1460       1470       1480       1490       1500
    RNTLIIYLDK VSHSEDDCLA FKVHQYFNVE LIQPGAVKVY AYYNLEESCT RFYHPEKEDG 1510       1520       1530       1540       1550       1560
    KLNKLCRDEL CRCAEENCFI QKSDDKVTLE ERLDKACEPG VDYVYKTRLV KVQLSNDFDE 1570       1580       1590       1600       1610       1620
    YIMAIEQTIK SGSDEVQVGQ QRTFISPIKC REALKLEEKK HYLMWGLSSD FWGEKPNLSY 1630       1640       1650       1660
    IIGKDTWVEH WPEEDECQDE ENQKQCQDLG AFTESMVVFG
```

FIG. 1B

```
            cctctccct ctgtccctct gtccctctga cactgcactg tcccagcacc
            12        20         30         40         50         60 atgggaccca cctcaggtcc cagcctgctg ctcctgctac taacccacct cccccctggct
70         80         90         100        110        120 ctggggagtc ccatgtactc tatcatcacc cccaacatct tgaggatgga gagcgaggag
130        140        150        160        170        180 accatggtgc tggaggccca cgacgcgcaa ggggatgttc cagtcactgt tactgtccac
190        200        210        220        230        240 gacatcccag gcaaaaaact agtgatgtcc agtgagaaga ctgtgctgac ccctgacacc
250        260        270        280        290        300 aaccacatgg gaaacgtcac cttcacgatc ccagccaaca gggagttcaa gtcagaaaag
310        320        330        340        350        360 gggcgcaaca agtacgtgac cgtgcaggcc accttcggga cccaagtggt ggagsaggtg
370        380        390        400        410        420 gtgctggtca gcctgcagag cgggtacctc tccatccaga cagacaagac catctacacc
430        440        450        460        470        480 cctggctcca cagttctcta taggatcttc accgecaacc acaagctgat acccgtgggc
490        500        510        520        530        540 cggacggtca tggtcaacat tgagaacccg gaaggcatcc cggtcaagca ggactccttg
550        560        570        580        590        600 tcttatcaga accagcttgg cgtcttgccc ttgtcttggg acattccgga actcgacaac
610        620        630        640        650        660 atgggccagt ggaagatccg agcctactat gcaaactcac cacagcaggt cttctccact
670        680        690        700        710        720 gagtttgagg tgaaggagta cgtgctgccc agtttcgagg tcatagtgga gactacagag
730        740        750        760        770        780 aaatcatact acatctataa cgagaagggc ctggaggtca ccatcacagc caggatcctc
790        800        810        820        830        840 taagggaaga aagtggaggg aactgccttt gtcatattcg ggatccagga tggcgaacag
850        860        870        880        890        900 aggattcccc tgcctgaatc cctcaagcgc atccgattg aggatgcctc ggggaggtt
910        920        930        940        950        960
```

FIG.2A

| | | | | | |
|---|---|---|---|---|---|
| gtgctgagcc | ggaaggtact | gctggacggg | gtgcagaacc | ccagagcaga | agacctggtg |
| 970 | 980 | 990 | 1000 | 1010 | 1020 |
| gggaagtctt | tgtacgtgtc | tgccaccgtc | atcttgaact | caggcagtga | catggtgcag |
| 1030 | 1040 | 1050 | 1060 | 1070 | 1080 |
| gcagagcgca | gcgggatccc | catcgtgacc | tctccctacc | agatccactt | caccaagaca |
| 1090 | 1100 | 1110 | 1120 | 1130 | 1140 |
| cccaagtact | tcaaaccagg | aatgcccttt | gacctcatgg | tgttcgtgac | gaaccctgat |
| 1150 | 1160 | 1170 | 1180 | 1190 | 1200 |
| ggatctccag | cctacagagt | ccaagtggca | gtccagggag | aggacactgt | gcagtctcta |
| 1210 | 1220 | 1230 | 1240 | 1250 | 1260 |
| acccagggag | atggcgtggc | caaactcagc | atcaacacac | accccagcca | gaagcccttg |
| 1270 | 1280 | 1290 | 1300 | 1310 | 1320 |
| agcatcacgg | tgcgcacgaa | gaagcaggag | ctctcggagg | cagagcaggc | taccaggacc |
| 1330 | 1340 | 1350 | 1360 | 1370 | 1380 |
| atgcaggctc | tgccctacag | caccgtgggc | aactccaaca | attacctgca | tctctcagtg |
| 1390 | 1400 | 1410 | 1420 | 1430 | 1440 |
| ctacgtacag | agatcagacc | cggggagacc | ctcaacgtca | acttcctcct | gcgaatggac |
| 1450 | 1460 | 1470 | 1480 | 1490 | 1500 |
| cgcgcccacg | aggccaagat | ccgctactac | acctacctga | tcatgaacaa | gggcaggctg |
| 1510 | 1520 | 1530 | 1540 | 1550 | 1560 |
| ttgaaggcgg | gacgccaggt | gcgagagccc | ggccaggacc | tggtggtgct | gcccctgtcc |
| 1570 | 1580 | 1590 | 1600 | 1610 | 1620 |
| atcaccaccg | acttcatccc | tcccttccgc | ctggtggcgt | actacacgct | gatcggtgcc |
| 1630 | 1640 | 1650 | 1660 | 1670 | 1680 |
| agcggccaga | gggaggtggt | ggccgactcc | gtgtgggtgg | acgtcaagga | ctcctgcgtg |
| 1690 | 1700 | 1710 | 1720 | 1730 | 1740 |
| ggctcgctgg | tggtaaaaag | cggccagtca | gaagaccggc | agcctgtacc | tgggcagcag |
| 1750 | 1760 | 1770 | 1780 | 1790 | 1800 |
| atgaccctga | agatagaggg | tgaccacggg | gcccgggtgg | tactggtggc | cgtggacaag |
| 1810 | 1820 | 1830 | 1840 | 1850 | 1860 |
| ggcgtgttcg | tgctgaataa | gaagaacaaa | ctgacgcaga | gtaagatctg | ggacgtggtg |
| 1870 | 1880 | 1890 | 1900 | 1910 | 1920 |

FIG.2B

```
gagaaggcag acatcggctg caccccgggc agtgggaagg attacgccgg tgtcttctcc
     1930       1940       1950       1960       1970       1980 gacgcagggc tgaccttcac gagcagcagt ggccagcaga ccgcccagag ggcagaactt
     1990       2000       2010       2020       2030       2040 cagtgcccgc agccagccgc ccgccgacgc cgttccgtgc agctcacgga gaagcgaatg
     2050       2060       2070       2080       2090       2100 gacaaagtcg gcaagtaccc caaggagctg cgcaagtgct gcgaggaccg catgcgggag
     2110       2120       2130       2140       2150       2160 aaccccatga ggttctcgtg ccagcgccgg acccgttcca tctccctggg cgaggcgtgc
     2170       2180       2190       2200       2210       2220 aagaaggtct tcctggactg ctgcaactac atcacagagc tgcggcggca gcacgcgcgg
     2230       2240       2250       2260       2270       2280 gccagccacc tgggcctggc caggagtaac ctggatgagg acatcattgc agaagagaac
     2290       2300       2310       2320       2330       2340 atcgtttccc gaagtgagtt cccagagagc tggctgtgga acgttgagga cttgaaagag
     2350       2360       2370       2380       2390       2400 ccaccgaaaa atggaatctc tacgaagctc atgaatatat ttttgaaaga ctccatcacc
     2410       2420       2430       2440       2450       2460 acgtggggaga ttctggctgt gagcatgtcg gacaagaaag ggatctgtgt ggcagacccc
     2470       2480       2490       2500       2510       2520 ttcgaggtca cagtaatgca ggacttcttc atcgacctgc ggctacccta ctctgttgtt
     2530       2540       2550       2560       2570       2580
```

FIG.2C

| | | | | | |
|---|---|---|---|---|---|
| cgaaacgagc | aggtggaaat | ccgagccgtt | ctctacaatt | accggcagaa | ccaagagctc |
| 2590 | 2600 | 2610 | 2620 | 2630 | 2640 |
| aaggtgaggg | tggaactact | ccacaatcca | gccttctgca | gcctggccac | caccaagagg |
| 2650 | 2660 | 2670 | 2680 | 2690 | 2700 |
| cgtcaccagc | agaccataac | catccccccc | aagtcctcgt | tgtccgttcc | atatgtcatc |
| 2710 | 2720 | 2730 | 2740 | 2750 | 2760 |
| gtgccgctaa | agaccggcct | gcaggaagtg | gaagtcaagg | ctgctgtcta | ccatcatttc |
| 2770 | 2780 | 2790 | 2800 | 2810 | 2820 |
| atcagtgacg | gtgtcaggaa | gtccctgaag | gtcgtgccgg | aaggaatcag | aatgaacaaa |
| 2830 | 2840 | 2850 | 2860 | 2870 | 2880 |
| actgtggctg | ttcgcaccct | ggatccagaa | cgcctgggcc | gtgaaggagt | gcagaaagag |
| 2890 | 2900 | 2910 | 2920 | 2930 | 2940 |
| gacatcccac | ctgcagacct | cagtgaccaa | gtcccggaca | ccgagtctga | gaccagaatt |
| 2950 | 2960 | 2970 | 2980 | 2990 | 3000 |
| ctcctgcaag | ggaccccagt | ggcccagatg | acagaggatg | ccgtcgacgc | ggaacggctg |
| 3010 | 3020 | 3030 | 3040 | 3050 | 3060 |
| aagcacctca | ttgtgacccc | ctcgggctgc | ggggaacaga | acatgatcgg | catgacgccc |
| 3070 | 3080 | 3090 | 3100 | 3110 | 3120 |
| acggtcatcg | ctgtgcatta | cctggatgaa | acggagcagt | gggagaagtt | cggcctagag |
| 3130 | 3140 | 3150 | 3160 | 3170 | 3180 |
| aagcggcagg | gggccttgga | gctcatcaag | aaggggtaca | cccagcagct | ggacttcaga |
| 3190 | 3200 | 3210 | 3220 | 3230 | 3240 |
| caacccagct | ctgcctttgc | ggccttcgtg | aaacgggcac | ccagcacctg | gctgaccgcc |
| 3250 | 3260 | 3270 | 3280 | 3290 | 3300 |
| tacgtggtca | aggtcttctc | tctggctgtc | aacctcatcg | ccatcgactc | ccaagtcctc |
| 3310 | 3320 | 3330 | 3340 | 3350 | 3360 |
| tgcggggctg | ttaaatggct | gatcctggag | aagcagaagc | ccgacggggt | cttccaggag |
| 3370 | 3380 | 3390 | 3400 | 3410 | 3420 |
| gatgcgcccg | tgatacacca | agaaatgatt | ggtggattac | ggaacaacaa | cgagaaagac |
| 3430 | 3440 | 3450 | 3460 | 3170 | 3480 |
| atggccctca | cggcctttgt | tctcatctcg | ctgcaggagg | ctaaagatat | ttgcgaggag |
| 3490 | 3500 | 3510 | 3520 | 3530 | 3540 |

FIG.2D

```
caggtcaaca gcctgccagg cagcatcact aaagcaggag acttccttga agccaactac
     3550       3560       3570       3580       3590       3600 atgaacctac agagatccta cactgtggcc attgctggct atgctctggc ccagatgggc
     3610       3620       3630       3640       3650       3660 aggctgaagg ggcctcttct taacaaattt ctgaccacag ccaaagataa gaaccgctgg
     3670       3680       3690       3700       3710       3720 gaggaccctg gtaagcagct ctacaacgtg gaggccacat cctatgccct cttggcccta
     3730       3740       3750       3760       3770       3780 ctgcagctaa aagactttga ctttgtgcct cccgtcgtgc gttggctcaa tgaacagaga
     3790       3800       3810       3820       3830       3840 tactacggtg gtggctatgg ctctacccag gccaccttca tggtgttcca agccttggct
     3850       3860       3870       3880       3890       3900 caataccaaa aggacgcccc tgaccaccag gaactgaacc ttgatgtgtc cctccaactg
     3910       3920       3930       3940       3950       3960 cccagccgca gctccaagat cacccaccgt atccactggg aatctgccag cctcctgcga
     3970       3980       3990       4000       4010       4020 tcagaagaga ccaaggaaaa tgagggtttc acagtcacag ctgaaggaaa aggccaaggc
     4030       4040       4050       4060       4070       4080 accttgtcgg tggtgacaat gtaccatgct aaggccaaag atcaactcac ctgtaataaa
     4090       4100       4110       4120       4130       4140 ttcgacctca aggtcaccat aaaaccagca ccggaaacag aaaagaggcc tcaggatgcc
     4150       4160       4170       4180       4190       4200 aagaacacta tgatccttga gatctgtacc aggtaccggg gagaccagga tgccactatg
     4210       4220       4230       4240       4250       4260 tctatattgg acatatccat gatgactggc tttgctccag acacagatga cctgaagcag
     4270       4280       4290       4300       4310       4320 ctggccaatg gtgttgacag atacatctcc aagtatgagc tggacaaagc cttctccgat
     4330       4340       4350       4360       4370       4380 aggaacaccc tcatcatcta cctggacaag gtctcacact ctgaggatga ctgtctagct
     4390       4400       4410       4420       4430       4440 ttcaaagttc accaatactt taatgtagag cttatccagc ctggagcagt caaggtctac
     4450       4460       4470       4480       4490       4500
```

FIG.2E

```
gcctattaca acctggagga aagctgtacc cggttctacc atccggaaaa ggaggatgga
    4510       4520       4530       4540       4550       4560 aagctgaaca agctctgccg tgatgaactg tgccgctgtg ctgaggagaa ttgcttcata
    4570       4580       4590       4600       4610       4620 caaaagtcgg atgacaaggt caccctggaa gaacggctgg acaaggcctg tgagccagga
    4631       4640       4650       4660       4670       4680 gtggactatg tgtacaagac ccgactggtc aaggtacagc tgtccaatga ctttgacgag
    4691       4700       4710       4720       4730       4740 tacatcatgg ccattgagca gaccatcaag tcaggctcgg atgaggtgca ggttggacag
    4750       4760       4770       4780       4790       4800 cagcgcacgt tcatcagccc catcaagtgc agagaagccc tgaagctgga ggagaagaaa
    4810       4820       4830       4840       4850       4860 cactacctca tgtggggtct ctcctccgat ttctggggag agaagcccaa cctcagctac
    4870       4880       4890       4900       4910       4920 atcatcggga aggacacttg ggtggagcac tggcctgagg aggacgaatg ccaagacgaa
    4930       4940       4950       4960       4970       4980 gagaaccaga aacaatgcca ggacctcggc gccttcaccg agagcatggt tgtctttggg
    4990       5000       5010       5020       5030       5040 tgccccaact gaccacaccc ccattcc
    5050       5060
```

FIG.2F

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1663 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 1:

```
Met  Gly  Pro  Thr  Ser  Gly  Pro  Ser  Leu  Leu  Leu  Leu  Leu  Leu  Thr  His
 1             5                        10                       15

Leu  Pro  Leu  Ala  Leu  Gly  Ser  Pro  Met  Tyr  Ser  Ile  Ile  Thr  Pro  Asn
           20                       25                      30

Ile  Leu  Arg  Leu  Glu  Ser  Glu  Glu  Thr  Met  Val  Leu  Glu  Ala  His  Asp
           35                       40                      45

Ala  Gln  Gly  Asp  Val  Pro  Val  Thr  Val  Thr  Val  His  Asp  Phe  Pro  Gly
           50                       55                      60

Lys  Lys  Leu  Val  Leu  Ser  Ser  Glu  Lys  Thr  Val  Leu  Thr  Pro  Ala  Thr
 65                      70                       75                      80

Asn  His  Met  Gly  Asn  Val  Thr  Phe  Thr  Ile  Pro  Ala  Asn  Arg  Glu  Phe
                     85                        90                           95

Lys  Ser  Glu  Lys  Gly  Arg  Asn  Lys  Phe  Val  Thr  Val  Gln  Ala  Thr  Phe
               100                      105                     110

Gly  Thr  Gln  Val  Val  Glu  Lys  Val  Val  Leu  Val  Ser  Leu  Gln  Ser  Gly
               115                      120                     125

Tyr  Leu  Phe  Ile  Gln  Thr  Asp  Lys  Thr  Ile  Tyr  Thr  Pro  Gly  Ser  Thr
          130                      135                      140

Val  Leu  Tyr  Arg  Ile  Phe  Thr  Val  Asn  His  Lys  Leu  Leu  Pro  Val  Gly
145                      150                      155                     160
```

```
Arg Thr Val Met Val Asn Ile Glu Asn Pro Glu Gly Ile Pro Val Lys
                165             170                 175
Gln Asp Ser Leu Ser Ser Gln Asn Gln Leu Gly Val Leu Pro Leu Ser
            180             185                 190
Trp Asp Ile Pro Glu Leu Val Asn Met Gly Gln Trp Lys Ile Arg Ala
        195             200                 205
Tyr Tyr Glu Asn Ser Pro Gln Gln Val Phe Ser Thr Glu Phe Glu Val
    210             215                 220
Lys Glu Tyr Val Leu Pro Ser Phe Glu Val Ile Val Glu Pro Thr Glu
225             230             235                 240
Lys Phe Tyr Tyr Ile Tyr Asn Glu Lys Gly Leu Glu Val Thr Ile Thr
                245             250                 255
Ala Arg Phe Leu Tyr Gly Lys Lys Val Glu Gly Thr Ala Phe Val Ile
            260             265                 270
Phe Gly Ile Gln Asp Gly Glu Gln Arg Ile Ser Leu Pro Glu Ser Leu
        275             280                 285
Lys Arg Ile Pro Ile Glu Asp Gly Ser Gly Glu Val Val Leu Ser Arg
    290             295                 300
Lys Val Leu Leu Asp Gly Val Gln Asn Pro Arg Ala Glu Asp Leu Val
305             310             315                 320
Gly Lys Ser Leu Tyr Val Ser Ala Thr Val Ile Leu His Ser Gly Ser
                325             330                 335
Asp Met Val Gln Ala Glu Arg Ser Gly Ile Pro Ile Val Thr Ser Pro
            340             345                 350
Tyr Gln Ile His Phe Thr Lys Thr Pro Lys Tyr Phe Lys Pro Gly Met
        355             360                 365
Pro Phe Asp Leu Met Val Phe Val Thr Asn Pro Asp Gly Ser Pro Ala
    370             375                 380
Tyr Arg Val Pro Val Ala Val Gln Gly Glu Asp Thr Val Gln Ser Leu
385             390             395                 400
Thr Gln Gly Asp Gly Val Ala Lys Leu Ser Ile Asn Thr His Pro Ser
                405             410                 415
Gln Lys Pro Leu Ser Ile Thr Val Arg Thr Lys Lys Gln Glu Leu Ser
            420             425                 430
Glu Ala Glu Gln Ala Thr Arg Thr Met Gln Ala Leu Pro Tyr Ser Thr
        435             440                 445
Val Gly Asn Ser Asn Asn Tyr Leu His Leu Ser Val Leu Arg Thr Glu
    450             455                 460
Leu Arg Pro Gly Glu Thr Leu Asn Val Asn Phe Leu Leu Arg Met Asp
465             470             475                 480
Arg Ala His Glu Ala Lys Ile Arg Tyr Tyr Thr Tyr Leu Ile Met Asn
                485             490                 495
Lys Gly Arg Leu Leu Lys Ala Gly Arg Gln Val Arg Glu Pro Gly Gln
            500             505                 510
Asp Leu Val Val Leu Pro Leu Ser Ile Thr Thr Asp Phe Ile Pro Ser
        515             520                 525
Phe Arg Leu Val Ala Tyr Tyr Thr Leu Ile Gly Ala Ser Gly Gln Arg
    530             535                 540
Glu Val Val Ala Asp Ser Val Trp Val Asp Val Lys Asp Ser Cys Val
545             550             555                 560
Gly Ser Leu Val Val Lys Ser Gly Gln Ser Glu Asp Arg Gln Pro Val
                565             570                 575
Pro Gly Gln Gln Met Thr Leu Lys Ile Glu Gly Asp His Gly Ala Arg
            580             585                 590
```

```
Val  Val  Leu  Val  Ala  Val  Asp  Lys  Gly  Val  Phe  Val  Leu  Asn  Lys  Lys
          595            600                      605

Asn  Lys  Leu  Thr  Gln  Ser  Lys  Ile  Trp  Asp  Val  Val  Glu  Lys  Ala  Asp
     610                 615                      620

Ile  Gly  Cys  Thr  Pro  Gly  Ser  Gly  Lys  Asp  Tyr  Ala  Gly  Val  Phe  Ser
625                      630                 635                           640

Asp  Ala  Gly  Leu  Thr  Phe  Thr  Ser  Ser  Ser  Gly  Gln  Gln  Thr  Ala  Gln
               645                      650                           655

Arg  Ala  Glu  Leu  Gln  Cys  Pro  Gln  Pro  Ala  Ala  Arg  Arg  Arg  Arg  Ser
               660                 665                      670

Val  Gln  Leu  Thr  Glu  Lys  Arg  Met  Asp  Lys  Val  Gly  Lys  Tyr  Pro  Lys
          675                 680                      685

Glu  Leu  Arg  Lys  Cys  Cys  Glu  Asp  Gly  Met  Arg  Glu  Asn  Pro  Met  Arg
     690                 695                      700

Phe  Ser  Cys  Gln  Arg  Arg  Thr  Arg  Phe  Ile  Ser  Leu  Gly  Glu  Ala  Cys
705                      710                 715                           720

Lys  Lys  Val  Phe  Leu  Asp  Cys  Cys  Asn  Tyr  Ile  Thr  Glu  Leu  Arg  Arg
               725                      730                           735

Gln  His  Ala  Arg  Ala  Ser  His  Leu  Gly  Leu  Ala  Arg  Ser  Asn  Leu  Asp
               740                      745                      750

Glu  Asp  Ile  Ile  Ala  Glu  Glu  Asn  Ile  Val  Ser  Arg  Ser  Glu  Phe  Pro
          755                      760                 765

Glu  Ser  Trp  Leu  Trp  Asn  Val  Glu  Asp  Leu  Lys  Glu  Pro  Pro  Lys  Asn
     770                      775                      780

Gly  Ile  Ser  Thr  Lys  Leu  Met  Asn  Ile  Phe  Leu  Lys  Asp  Ser  Ile  Thr
785                      790                 795                           800

Thr  Trp  Glu  Ile  Leu  Ala  Val  Ser  Met  Ser  Asp  Lys  Lys  Gly  Ile  Cys
               805                      810                           815

Val  Ala  Asp  Pro  Phe  Glu  Val  Thr  Val  Met  Gln  Asp  Phe  Phe  Ile  Asp
                820                      825                      830

Leu  Arg  Leu  Pro  Tyr  Ser  Val  Val  Arg  Asn  Glu  Gln  Val  Glu  Ile  Arg
     835                      840                      845

Ala  Val  Leu  Tyr  Asn  Tyr  Arg  Gln  Asn  Gln  Glu  Leu  Lys  Val  Arg  Val
     850                      855                      860

Glu  Leu  Leu  His  Asn  Pro  Ala  Phe  Cys  Ser  Leu  Ala  Thr  Thr  Lys  Arg
865                      870                      875                      880

Arg  His  Gln  Gln  Thr  Ile  Thr  Ile  Pro  Pro  Lys  Ser  Ser  Leu  Ser  Val
                    885                      890                      895

Pro  Tyr  Val  Ile  Val  Pro  Leu  Lys  Thr  Gly  Leu  Gln  Glu  Val  Glu  Val
               900                 905                      910

Lys  Ala  Ala  Val  Tyr  His  His  Phe  Ile  Ser  Asp  Gly  Val  Arg  Lys  Ser
          915                      920                 925

Leu  Lys  Val  Val  Pro  Glu  Gly  Ile  Arg  Met  Asn  Lys  Thr  Val  Ala  Val
     930                      935                 940

Arg  Thr  Leu  Asp  Pro  Glu  Arg  Leu  Gly  Arg  Glu  Gly  Val  Gln  Lys  Glu
945                      950                      955                      960

Asp  Ile  Pro  Pro  Ala  Asp  Leu  Ser  Asp  Gln  Val  Pro  Asp  Thr  Glu  Ser
                    965                      970                      975

Glu  Thr  Arg  Ile  Leu  Leu  Gln  Gly  Thr  Pro  Val  Ala  Gln  Met  Thr  Glu
               980                      985                      990

Asp  Ala  Val  Asp  Ala  Glu  Arg  Leu  Lys  His  Leu  Ile  Val  Thr  Pro  Ser
          995                      1000                     1005

Gly  Cys  Gly  Glu  Gln  Asn  Met  Ile  Gly  Met  Thr  Pro  Thr  Val  Ile  Ala
```

```
                    1010                      1015                       1020
Val  His  Tyr  Leu  Asp  Glu  Thr  Glu  Gln  Trp  Glu  Lys  Phe  Gly  Leu  Glu
1025                     1030                      1035                      1040

Lys  Arg  Gln  Gly  Ala  Leu  Glu  Leu  Ile  Lys  Lys  Gly  Tyr  Thr  Gln  Gln
                    1045                      1050                      1055

Leu  Ala  Phe  Arg  Gln  Pro  Ser  Ser  Ala  Phe  Ala  Ala  Phe  Val  Lys  Arg
                    1060                      1065                      1070

Ala  Pro  Ser  Thr  Trp  Leu  Thr  Ala  Tyr  Val  Val  Lys  Val  Phe  Ser  Leu
                    1075                      1080                      1085

Ala  Val  Asn  Leu  Ile  Ala  Ile  Asp  Ser  Gln  Val  Leu  Cys  Gly  Ala  Val
                    1090                      1095                      1100

Lys  Trp  Leu  Ile  Leu  Glu  Lys  Gln  Lys  Pro  Asp  Gly  Val  Phe  Gln  Glu
1105                     1110                      1115                      1120

Asp  Ala  Pro  Val  Ile  His  Gln  Glu  Met  Ile  Gly  Gly  Leu  Arg  Asn  Asn
                    1125                      1130                      1135

Asn  Glu  Lys  Asp  Met  Ala  Leu  Thr  Ala  Phe  Val  Leu  Ile  Ser  Leu  Gln
                    1140                      1145                      1150

Glu  Ala  Lys  Asp  Ile  Cys  Glu  Glu  Gln  Val  Asn  Ser  Leu  Pro  Gly  Ser
                    1155                      1160                      1165

Ile  Thr  Lys  Ala  Gly  Asp  Phe  Leu  Glu  Ala  Asn  Tyr  Met  Asn  Leu  Gln
                    1170                      1175                      1180

Arg  Ser  Tyr  Thr  Val  Ala  Ile  Ala  Gly  Tyr  Ala  Leu  Ala  Gln  Met  Gly
1185                     1190                      1195                      1200

Arg  Leu  Lys  Gly  Pro  Leu  Leu  Asn  Lys  Phe  Leu  Thr  Thr  Ala  Lys  Asp
                    1205                      1210                      1215

Lys  Asn  Arg  Trp  Glu  Asp  Pro  Gly  Lys  Gln  Leu  Tyr  Asn  Val  Glu  Ala
                    1220                      1225                      1230

Thr  Ser  Tyr  Ala  Leu  Leu  Ala  Leu  Leu  Gln  Leu  Lys  Asp  Phe  Asp  Phe
                    1235                      1240                      1245

Val  Pro  Pro  Val  Val  Arg  Trp  Leu  Asn  Glu  Gln  Arg  Tyr  Tyr  Gly  Gly
                    1250                      1255                      1260

Gly  Tyr  Gly  Ser  Thr  Gln  Ala  Thr  Phe  Met  Val  Phe  Gln  Ala  Leu  Ala
1265                     1270                      1275                      1280

Gln  Tyr  Gln  Lys  Asp  Ala  Pro  Asp  His  Gln  Glu  Leu  Asn  Leu  Asp  Val
                    1285                      1290                      1295

Ser  Leu  Gln  Leu  Pro  Ser  Arg  Ser  Ser  Lys  Ile  Thr  His  Arg  Ile  His
                    1300                      1305                      1310

Trp  Glu  Ser  Ala  Ser  Leu  Leu  Arg  Ser  Glu  Glu  Thr  Lys  Glu  Asn  Glu
                    1315                      1320                      1325

Gly  Phe  Thr  Val  Thr  Ala  Glu  Gly  Lys  Gly  Gln  Gly  Thr  Leu  Ser  Val
                    1330                      1335                      1340

Val  Thr  Met  Tyr  His  Ala  Lys  Ala  Lys  Asp  Gln  Leu  Thr  Cys  Asn  Lys
1345                     1350                      1355                      1360

Phe  Asp  Leu  Lys  Val  Thr  Ile  Lys  Pro  Ala  Pro  Glu  Thr  Glu  Lys  Arg
                    1365                      1370                      1375

Pro  Gln  Asp  Ala  Lys  Asn  Thr  Met  Ile  Leu  Glu  Ile  Cys  Thr  Arg  Tyr
                    1380                      1385                      1390

Arg  Gly  Asp  Gln  Asp  Ala  Thr  Met  Ser  Ile  Leu  Asp  Ile  Ser  Met  Met
                    1395                      1400                      1405

Thr  Gly  Phe  Ala  Pro  Asp  Thr  Asp  Asp  Leu  Lys  Gln  Leu  Ala  Asn  Gly
                    1410                      1415                      1420

Val  Asp  Arg  Tyr  Ile  Ser  Lys  Tyr  Glu  Leu  Asp  Lys  Ala  Phe  Ser  Asp
1425                     1430                      1435                      1440
```

|  | Arg | Asn | Thr | Leu | Ile 1445 | Ile | Tyr | Leu | Asp | Lys 1450 | Val | Ser | His | Ser | Glu 1455 | Asp |
|---|---|---|---|---|---|---|---|---|---|---|---|---|---|---|---|---|
|  | Asp | Cys | Leu | Ala 1460 | Phe | Lys | Val | His | Gln 1465 | Tyr | Phe | Asn | Val | Glu 1470 | Leu | Ile |
|  | Gln | Pro | Gly 1475 | Ala | Val | Lys | Val | Tyr 1480 | Ala | Tyr | Tyr | Asn | Leu 1485 | Glu | Glu | Ser |
|  | Cys | Thr 1490 | Arg | Phe | Tyr | His | Pro 1495 | Glu | Lys | Glu | Asp | Gly 1500 | Lys | Leu | Asn | Lys |
|  | Leu 1505 | Cys | Arg | Asp | Glu | Leu 1510 | Cys | Arg | Cys | Ala | Glu 1515 | Glu | Asn | Cys | Phe | Ile 1520 |
|  | Gln | Lys | Ser | Asp | Asp 1525 | Lys | Val | Thr | Leu | Glu 1530 | Glu | Arg | Leu | Asp | Lys 1535 | Ala |
|  | Cys | Glu | Pro | Gly | Val 1540 | Asp | Tyr | Val | Tyr | Lys 1545 | Thr | Arg | Leu | Val | Lys 1550 | Val |
|  | Gln | Leu | Ser 1555 | Asn | Asp | Phe | Asp | Glu 1560 | Tyr | Ile | Met | Ala | Ile 1565 | Glu | Gln | Thr |
|  | Ile | Lys | Ser 1570 | Gly | Ser | Asp | Glu | Val 1575 | Gln | Val | Gly | Gln | Gln 1580 | Arg | Thr | Phe |
|  | Ile | Ser | Pro | Ile | Lys 1585 | Cys | Arg | Glu | Ala | Leu 1590 | Leu | Lys | Leu | Glu | Glu 1595 | Lys | Lys 1600 |
|  | His | Tyr | Leu | Met | Trp 1605 | Gly | Leu | Ser | Ser | Asp 1610 | Phe | Trp | Gly | Glu | Lys 1615 | Pro |
|  | Asn | Leu | Ser | Tyr | Ile 1620 | Ile | Gly | Lys | Asp | Thr 1625 | Trp | Val | Glu | His | Trp 1630 | Pro |
|  | Glu | Glu | Asp | Glu | Cys 1635 | Gln | Asp | Glu | Glu | Asn 1640 | Gln | Lys | Gln | Cys 1645 | Gln | Asp |
|  | Leu | Gly | Ala | Phe | Thr 1650 | Glu | Ser | Met | Val | Val 1655 | Phe | Gly | Cys | Pro 1660 | Asn |  |

( 2 ) INFORMATION FOR SEQ ID NO: 2:

( i ) SEQUENCE CHARACTERISTICS:
        ( A ) LENGTH: 5056 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 2:

```
CCTCTCCCTC  TGTCCCTCTG  TCCCTCTGAC  CCTGCACTGT  CCCAGCACCA  TGGGACCCAC    60
CTCAGGTCCC  AGCCTGCTGC  TCCTGCTACT  AACCCACCTC  CCCCTGGCTC  TGGGGAGTCC   120
CATGTACTCT  ATCATCACCC  CCAACATCTT  GCGGCTGGAG  AGCGAGGAGA  CCATGGTGCT   180
GGAGGCCCAC  GACGCGCAAG  GGGATGTTCC  AGTCACTGTT  ACTGTCCACG  ACTTCCCAGG   240
CAAAAAACTA  GTGCTGTCCA  GTGAGAAGAC  TGTGCTGACC  CCTGCCACCA  ACCACATGGG   300
CAACGTCACC  TTCACGATCC  CAGCCAACAG  GGAGTTCAAG  TCAGAAAAGG  GGCGCAACAA   360
GTTCGTGACC  GTGCAGGCCA  CCTTCGGGAC  CCAAGTGGTG  GAGAAGGTGG  TGCTGGTCAG   420
CCTGCAGAGC  GGGTACCTCT  TCATCCAGAC  AGACAAGACC  ATCTACACCC  CTGGCTCCAC   480
AGTTCTCTAT  CGGATCTTCA  CCGTCAACCA  CAAGCTGCTA  CCCGTGGGCC  GGACGGTCAT   540
GGTCAACATT  GAGAACCCGG  AAGGCATCCC  GGTCAAGCAG  GACTCCTTGT  CTTCTCAGAA   600
CCAGCTTGGC  GTCTTGCCCT  TGTCTTGGGA  CATTCCGGAA  CTCGTCAACA  TGGGCCAGTG   660
GAAGATCCGA  GCCTACTATG  AAAACTCACC  ACAGCAGGTC  TTCTCCACTG  AGTTTGAGGT   720
GAAGGAGTAC  GTGCTGCCCA  GTTTCGAGGT  CATAGTGGAG  CCTACAGAGA  AATTCTACTA   780
```

| | | | | | | |
|---|---|---|---|---|---|---|
| CATCTATAAC | GAGAAGGGCC | TGGAGGTCAC | CATCACCGCC | AGGTTCCTCT | ACGGGAAGAA | 840 |
| AGTGGAGGGA | ACTGCCTTTG | TCATCTTCGG | GATCCAGGAT | GGCGAACAGA | GGATTTCCCT | 900 |
| GCCTGAATCC | CTCAAGCGCA | TTCCGATTGA | GGATGGCTCG | GGGGAGGTTG | TGCTGAGCCG | 960 |
| GAAGGTACTG | CTGGACGGGG | TGCAGAACCC | CCGAGCAGAA | GACCTGGTGG | GGAAGTCTTT | 1020 |
| GTACGTGTCT | GCCACCGTCA | TCTTGCACTC | AGGCAGTGAC | ATGGTGCAGG | CAGAGCGCAG | 1080 |
| CGGGATCCCC | ATCGTGACCT | CTCCCTACCA | GATCCACTTC | ACCAAGACAC | CAAGTACTT | 1140 |
| CAAACCAGGA | ATGCCCTTTG | ACCTCATGGT | GTTCGTGACG | AACCCTGATG | GCTCTCCAGC | 1200 |
| CTACCGAGTC | CCCGTGGCAG | TCCAGGGCGA | GGACACTGTG | CAGTCTCTAA | CCCAGGGAGA | 1260 |
| TGGCGTGGCC | AAACTCAGCA | TCAACACACA | CCCCAGCCAG | AAGCCCTTGA | GCATCACGGT | 1320 |
| GCGCACGAAG | AAGCAGGAGC | TCTCGGAGGC | AGAGCAGGCT | ACCAGGACCA | TGCAGGCTCT | 1380 |
| GCCCTACAGC | ACCGTGGGCA | ACTCCAACAA | TTACCTGCAT | CTCTCAGTGC | TACGTACAGA | 1440 |
| GCTCAGACCC | GGGGAGACCC | TCAACGTCAA | CTTCCTCCTG | CGAATGGACC | GCGCCCACGA | 1500 |
| GGCCAAGATC | CGCTACTACA | CCTACCTGAT | CATGAACAAG | GGCAGGCTGT | TGAAGGCGGG | 1560 |
| ACGCCAGGTG | CGAGAGCCCG | GCCAGGACCT | GGTGGTGCTG | CCCCTGTCCA | TCACCACCGA | 1620 |
| CTTCATCCCT | TCCTTCCGCC | TGGTGGCGTA | CTACACGCTG | ATCGGTGCCA | GCGGCCAGAG | 1680 |
| GGAGGTGGTG | GCCGACTCCG | TGTGGGTGGA | CGTCAAGGAC | TCCTGCGTGG | GCTCGCTGGT | 1740 |
| GGTAAAAAGC | GGCCAGTCAG | AAGACCGGCA | GCCTGTACCT | GGGCAGCAGA | TGACCCTGAA | 1800 |
| GATAGAGGGT | GACCACGGGG | CCCGGGTGGT | ACTGGTGGCC | GTGGACAAGG | GCGTGTTCGT | 1860 |
| GCTGAATAAG | AAGAACAAAC | TGACGCAGAG | TAAGATCTGG | GACGTGGTGG | AGAAGGCAGA | 1920 |
| CATCGGCTGC | ACCCCGGGCA | GTGGGAAGGA | TTACGCCGGT | GTCTTCTCCG | ACGCAGGGCT | 1980 |
| GACCTTCACG | AGCAGCAGTG | GCCAGCAGAC | CGCCCAGAGG | GCAGAACTTC | AGTGCCCGCA | 2040 |
| GCCAGCCGCC | CGCCGACGCC | GTTCCGTGCA | GCTCACGGAG | AAGCGAATGG | ACAAAGTCGG | 2100 |
| CAAGTACCCC | AAGGAGCTGC | GCAAGTGCTG | CGAGGACGGC | ATGCGGGAGA | CCCCATGAG | 2160 |
| GTTCTCGTGC | CAGCGCCGGA | CCCGTTTCAT | CTCCCTGGGC | GAGGCGTGCA | AGAAGGTCTT | 2220 |
| CCTGGACTGC | TGCAACTACA | TCACAGAGCT | GCGGCGGCAG | CACGCGCGGG | CCAGCCACCT | 2280 |
| GGGCCTGGCC | AGGAGTAACC | TGGATGAGGA | CATCATTGCA | GAAGAGAACA | TCGTTTCCCG | 2340 |
| AAGTGAGTTC | CCAGAGAGCT | GGCTGTGGAA | CGTTGAGGAC | TTGAAAGAGC | CACCGAAAAA | 2400 |
| TGGAATCTCT | ACGAAGCTCA | TGAATATATT | TTTGAAAGAC | TCCATCACCA | CGTGGGAGAT | 2460 |
| TCTGGCTGTG | AGCATGTCGG | ACAAGAAAGG | GATCTGTGTG | GCAGACCCCT | TCGAGGTCAC | 2520 |
| AGTAATGCAG | GACTTCTTCA | TCGACCTGCG | GCTACCCTAC | TCTGTTGTTC | GAAACGAGCA | 2580 |
| GGTGGAAATC | CGAGCCGTTC | TCTACAATTA | CCGGCAGAAC | CAAGAGCTCA | AGGTGAGGGT | 2640 |
| GGAACTACTC | CACAATCCAG | CCTTCTGCAG | CCTGGCCACC | ACCAAGAGGC | GTCACCAGCA | 2700 |
| GACCATAACC | ATCCCCCCCA | AGTCCTCGTT | GTCCGTTCCA | TATGTCATCG | TGCCGCTAAA | 2760 |
| GACCGGCCTG | CAGGAAGTGG | AAGTCAAGGC | TGCTGTCTAC | CATCATTTCA | TCAGTGACGG | 2820 |
| TGTCAGGAAG | TCCCTGAAGG | TCGTGCCGGA | AGGAATCAGA | ATGAACAAAA | CTGTGGCTGT | 2880 |
| TCGCACCCTG | GATCCAGAAC | GCCTGGGCCG | TGAAGGAGTG | CAGAAAGAGG | ACATCCCACC | 2940 |
| TGCAGACCTC | AGTGACCAAG | TCCCGGACAC | CGAGTCTGAG | ACCAGAATTC | TCCTGCAAGG | 3000 |
| GACCCCAGTG | GCCCAGATGA | CAGAGGATGC | CGTCGACGCG | GAACGGCTGA | AGCACCTCAT | 3060 |
| TGTGACCCCC | TCGGGCTGCG | GGAACAGAA | CATGATCGGC | ATGACGCCCA | CGGTCATCGC | 3120 |
| TGTGCATTAC | CTGGATGAAA | CGGAGCAGTG | GGAGAAGTTC | GGCCTAGAGA | AGCGGCAGGG | 3180 |

```
GGCCTTGGAG CTCATCAAGA AGGGGTACAC CCAGCAGCTG GCCTTCAGAC AACCCAGCTC    3240
TGCCTTTGCG GCCTTCGTGA AACGGGCACC CAGCACCTGG CTGACCGCCT ACGTGGTCAA    3300
GGTCTTCTCT CTGGCTGTCA ACCTCATCGC CATCGACTCC CAAGTCCTCT GCGGGGCTGT    3360
TAAATGGCTG ATCCTGGAGA AGCAGAAGCC CGACGGGTC TTCCAGGAGG ATGCGCCCGT     3420
GATACACCAA GAAATGATTG GTGGATTACG GAACAACAAC GAGAAAGACA TGGCCCTCAC    3480
GGCCTTTGTT CTCATCTCGC TGCAGGAGGC TAAAGATATT GCGAGGAGC AGGTCAACAG     3540
CCTGCCAGGC AGCATCACTA AAGCAGGAGA CTTCCTTGAA GCCAACTACA TGAACCTACA    3600
GAGATCCTAC ACTGTGGCCA TTGCTGGCTA TGCTCTGGCC CAGATGGGCA GGCTGAAGGG    3660
GCCTCTTCTT AACAAATTTC TGACCACAGC CAAAGATAAG AACCGCTGGG AGGACCCTGG    3720
TAAGCAGCTC TACAACGTGG AGGCCACATC CTATGCCCTC TTGGCCCTAC TGCAGCTAAA    3780
AGACTTTGAC TTTGTGCCTC CCGTCGTGCG TTGGCTCAAT GAACAGAGAT ACTACGGTGG    3840
TGGCTATGGC TCTACCCAGG CCACCTTCAT GGTGTTCCAA GCCTTGGCTC AATACCAAAA    3900
GGACGCCCCT GACCACCAGG AACTGAACCT TGATGTGTCC CTCCAACTGC CCAGCCGCAG    3960
CTCCAAGATC ACCCACCGTA TCCACTGGGA ATCTGCCAGC CTCCTGCGAT CAGAAGAGAC    4020
CAAGGAAAAT GAGGGTTTCA CAGTCACAGC TGAAGGAAAA GGCCAAGGCA CCTTGTCGGT    4080
GGTGACAATG TACCATGCTA AGGCCAAAGA TCAACTCACC TGTAATAAAT TCGACCTCAA    4140
GGTCACCATA AAACCAGCAC CGGAAACAGA AAAGAGGCCT CAGGATGCCA AGAACACTAT    4200
GATCCTTGAG ATCTGTACCA GGTACCGGGG AGACCAGGAT GCCACTATGT CTATATTGGA    4260
CATATCCATG ATGACTGGCT TTGCTCCAGA CACAGATGAC CTGAAGCAGC TGGCCAATGG    4320
TGTTGACAGA TACATCTCCA AGTATGAGCT GGACAAAGCC TTCTCCGATA GGAACACCCT    4380
CATCATCTAC CTGGACAAGG TCTCACACTC TGAGGATGAC TGTCTAGCTT TCAAAGTTCA    4440
CCAATACTTT AATGTAGAGC TTATCCAGCC TGGAGCAGTC AAGGTCTACG CCTATTACAA    4500
CCTGGAGGAA AGCTGTACCC GGTTCTACCA TCCGGAAAAG GAGGATGGAA AGCTGAACAA    4560
GCTCTGCCGT GATGAACTGT GCCGCTGTGC TGAGGAGAAT TGCTTCATAC AAAAGTCGGA    4620
TGACAAGGTC ACCCTGGAAG AACGGCTGGA CAAGGCCTGT GAGCCAGGAG TGGACTATGT    4680
GTACAAGACC CGACTGGTCA AGGTTCAGCT GTCCAATGAC TTTGACGAGT ACATCATGGC    4740
CATTGAGCAG ACCATCAAGT CAGGCTCGGA TGAGGTGCAG GTTGGACAGC AGCGCACGTT    4800
CATCAGCCCC ATCAAGTGCA GAGAAGCCCT GAAGCTGGAG GAGAAGAAAC ACTACCTCAT    4860
GTGGGGTCTC TCCTCCGATT TCTGGGGAGA GAAGCCCAAC CTCAGCTACA TCATCGGGAA    4920
GGACACTTGG GTGGAGCACT GGCCTGAGGA GGACGAATGC CAAGACGAAG AGAACCAGAA    4980
ACAATGCCAG GACCTCGGCG CCTTCACCGA GAGCATGGTT GTCTTTGGGT GCCCCAACTG    5040
ACCACACCCC CATTCC                                                   5056
```

MODIFIED HUMAN C3 PROTEINS

This application is a continuation, of application Ser. No. PCT/GB95/02121, filed 8 Sep., 1995.

The present invention relates to novel modified proteins capable of forming stable C3 convertases, DNA sequences encoding such proteins and the use of such proteins as therapeutic agents, particularly for use in depleting levels of complement pathway proteins.

The complement system functions in the immune response of humans and other vertebrates, being of major importance in the effector functions such as phagocytosis, cytolysis and recruitment of cells that induce local inflammatory responses [15]. These properties are desirable for elimination of invading pathogens, such as bacteria, but undesirable when triggered to act against host tissues (e.g. in post-ischemic reperfusion injury [3]) or against foreign therapeutic material (e.g. hyperacute rejection of xenografts [7]). There have been attempts to abrogate these undesirable properties by exploiting derivatives of complement regulatory proteins whose normal function is to suppress complement activation [10, 18].

The complement system comprises proteins both on the surface of cells, (receptors and regulators) as well as in the fluid-phase (blood plasma and other extracellular environments). The critical step for the generation of responses is the proteolytic conversion of C3 to the fragments C3b and C3a. C3a is an anaphylatoxin that, like C5a, attracts mast cells to the site of challenge, resulting in local release of histamine, vasodilation and other inflammatory effects. The nascent C3b has an ability to bind to surfaces around its site of generation. This C3b then focuses attack by the cytolytic complement components (C5–C9).

Surface-bound C3b, and its degradation products, also function as ligands for C3 receptors mediating, for example, phagocytosis [15]. There are two distinct pathways of complement activation that both result in conversion of C3 to C3b and subsequent responses. The classical pathway is commonly triggered by complexes of antibody with antigen, initiating an enzyme cascade involving the proteins C1q, C1r, C1s, C2 and C4. The alternative pathway depends on an activation loop involving C3 itself and requiring factors B and D.

Conversion of C3 to C3b (or C3i) produces a product that can combine with factor B, giving C3bB (or C3iB). These complexes are acted upon by factor D to generate C3bBb, which is a C3 convertase capable of cleaving more C3 to C3b, leading to more C3bBb and even more C3 conversion. Under certain circumstances the C3bBb complex is stabilised by association with the positive regulator properdin (P). However, this positive-feedback loop is normally limited to a slow tick-over by regulatory proteins, notably factor H and factor I.

Factor H (and structurally related cell-associated molecules) (i) displaces B and Bb from C3b, and (ii) acts as a cofactor for factor I which cleaves C3b into iC3b thereby preventing any recombination with factor B to form more C3 convertases. The pathway is "fired" into amplified generation of C3b in the presence of surfaces, such as many bacterial cell walls, that bind nascent C3b and impede its regulation by factors H and I. Nascent C3b is also able to bind to endogenous cells. Endogenous cell surfaces normally exposed to complement are therefore additionally protected by membrane-bound regulators such as MCP, DAF and CR1 acting in a similar manner to factor H.

There are a few rare naturally occurring conditions where the normal fluid-phase regulation cannot occur and spontaneous C3 conversion ultimately results in generalised depletion of C3 from the circulation: (i) genetic deficiencies of factor H or I [13], (ii) the presence of antibodies (nephritic factors) that bind to C3bBb and impede dissociation [4], and (iii) contact with a protein in cobra venom, called cobra venom factor (CVF), that combines with factor B and forms a C3 convertase enzyme which does not contain C3b and is not affected by factors H and I [14]. These illustrate the normal physiological importance of down-regulation of complement in the absence of specific activation.

There are also circumstances where specific activation occurs, but is unwanted, particularly when it is directed against tissues of the host (e.g. tissue damaged by ischemia or surgery) or against foreign material deliberately given for therapeutic purposes (such as a xenograft, artificial organ or a dialysis membrane). The complement activation results in undesirable attack and further damage, so in these cases it would be beneficial to block or inhibit the activation and response.

Existing approaches to preventing complement-mediated damage have targeted the use of down-regulatory proteins (CR1, MCP, DAF and factors H and I) to inhibit complement activation. Complement inhibitors like factor I, factor H and soluble derivatives of the membrane-bound proteins CR1, DAF, MCP do suppress the fluid-phase amplification loop of the alternative pathway. Therefore there have been attempts to use these molecules, particularly CR1 (which seems to be the most potent) to reduce complement-mediated damage in models of physiological situations [10, 18].

Factor H is endogenously present in blood plasma in high concentrations (typically 0.3–0.5 mg/ml [15]), so even though increased levels of inhibitors do dampen-down fluid-phase reactions, their potency is weak so large amounts of purified proteins would have to be administered in vivo (e.g probably in excess of 5 mg/Kg body weight of soluble CR1). In addition, the alternative pathway is activated by surfaces where the effect of factor H is already impeded. While this does not necessarily concomitantly reduce the activities of other inhibitors, the same factors suggest that they are unlikely to be completely or universally effective.

Cobra Venom Factor(CVF) has the property of generating a stable C3 convertase which can be used experimentally to deplete complement in animals in vivo, and in other samples (e.g. human blood plasma) in vitro. CVF is potent (e.g. 40 $\mu$g/Kg can destroy the complement activity of a mouse [16]). However, there are disadvantages that make it unsuitable for therapeutic use in humans.

Firstly, it is obtained from cobra venom (a difficult source to obtain and dangerous to handle) and must therefore be carefully purified from the venom neurotoxins. There is also the obvious difficulty in obtaining supplies. This problem cannot readily be overcome by cloning and expressing the gene ex vivo, because there are post-translational modifications that occur in the snake (specific proteolytic processing) that may be difficult (or impossible) to reproduce in vitro.

In addition, the enzymes and digestion conditions required for this processing are currently unknown. Secondly, the protein is of foreign origin (to humans) and therefore immunogenic. This precludes its repeated therapeutic use, as would be required to decomplement a patient over many weeks (e.g. to allow xenograft survival).

Although CVF has some structural and functional homologies with human C3 [17], it also has major differences in both respects (e.g. chain structure, site of biosynthesis, insensitivity to complement regulators, formation of a stable C3 convertase). It is not derived from the cobra equivalent of C3 which is known, having been cloned and sequenced, and which in gross structure and function resembles human C3 more closely than does CVF [8].

CVF is a venom-specific product of an animal of great evolutionary distance from homo sapiens. It is therefore not practicable to use genetic manipulation to modify this protein into a product that can be used non-immunogenically in humans.

We have now devised an alternative strategy which relies on by-passing the physiological regulation and, instead of inhibiting complement activation, causes the system to be super-activated. This has two applications. Firstly, it can be used in vivo to activate complement until one or more components are exhausted, resulting in loss of ability to produce local responses to any subsequent challenge (such as a xenograft). Secondly, the unregulated super-activation can be deliberately localised to a particular target (e.g. a virus or a virally-infected cell) to increase the sensitivity of that target to complement-mediated destructive responses.

The term "regulators of complement activation" is used herein to include all proteins that act to inhibit amplification of C3 conversion, and is not intended to be resticted in meaning to those proteins whose genes are located in the RCA genetic locus. It does not however include "up-regulators" such as properdin. "C3 conversion" is defined as the proteolytic conversion of C3 into C3b and C3a, unless otherwise indicated, and "C3 convertase" (or simply "convertase") is defined as an enzyme (typically a complex of two or more protein components; for example C3bBb, C3iBb, CVFBb or C4b2a) that catalyses this reaction.

Thus, in a first aspect the invention provides a native complement pathway protein modified such that the protein is capable of forming a stable C3 convertase.

By "native" is meant naturally occurring, ie is obtainable in nature. Thus, the definition encompasses any naturally occurring complement pathway protein modified as defined above. It is not intended to be restricted to species specific proteins. In other words, a modified human protein could be used as a stable C3 convertase in other mammalian species, for example. Typically, modified complement pathway proteins from the same species will be used.

Modification of the C3 DNA coding sequence, for example using site directed mutagenesis, can produce a variant of C3 that is resistant to complement regulatory proteins while retaining positive functional properties (cleavage to C3b by C3 convertase) and features of structural integrity (correct chain structure, and presence of a thiolester bond). The invention described herein relates to genetically-modified forms of native complement proteins, for example human C3, whose C3b fragment acquires the property of being resistant to physiological complement regulation. Because of this resistance, these molecules can generate stabilised forms of the corresponding C3 convertase that produce amplified conversion of C3 to C3b, and later degradation products, in physiological environments (e.g. in vivo).

In a preferred embodiment the invention provides a modified human C3 protein which is resistant to cleavage by factor I.

This can be achieved by modifying residues of the protein at proteolytic sites.

A particularly preferred embodiment of the invention relates to a modified human C3 protein wherein the protein is modified by replacement of either Arg-1303, Arg-1320 or both by another amino acid. The other amino acid may be Tyrosine, Cystine, Tryptophan, Glutamine, Glutamic acid or Glycine. Arg-1303 is preferably replaced by Glutamic acid or Glycine (less preferably by Glutamine). Arg-1320 is preferably replaced by Glutamine.

Other stategies for producing suitable modified proteins of the invention include:
  i) Reduced susceptibility to the inhibitory actions of factor H and related proteins (eg. MCP, DAF, CR1). For example, in human C3 residues 767–776 and 1209–1271 have been implicated in factor H binding [20,24], and substitution of one or more of these residues or other residues also associated with the action of these proteins, could reduce the binding of one or more of these regulatory proteins.
  ii) Reduced rate of dissociation of C3bBb. Mutations can be introduced which would strengthen the interaction between C3b and Bb. This would result in both a reduction in spontaneous decomposition of the enzyme, and diminish the effectiveness of factor H(and related regulators) in displacing Bb from C3b.

These mutations are desirable to reduce the rates of both the spontaneous and the factor H-mediated decomposition of C3bBb. Even in the absence of factor H, the fluid phase C3bBb complex has a half-life of only about 10 mins at 37° C. in the presence of properdin [6].

iii) Human C3 residues 752–761 are implicated in binding factor B. It is a highly conserved region in C3, and a closely related seqence is found in C4. As C4 binds the factor B homolog C2, the strong similarity of this region between C3 and C4, together with its high conservation in C3, further supports its role in C3 as a factor B binding site. Thus, changes in this region could have effects on B affinity and on the stability of C3bBb.
  iv) Resistance to other regulators of complement activation such as CR1, DAF and MCP would also be desirable. The mode of action of these regulators are all similar to factor H, so additional mutagenesis would not necessarily be required. Similarly, some pathogenic organisms express their own inhibitors of complement activation that are often structurally and functionally homologous to factor H (e.g. Vaccinia virus secretory peptide []). These molecules protect the invaders against immune responses, and it would be advantageous to be able to attack them with targeted C3 convertase enzymes resistant to these defences.
  v) Mutations that increase the stabilisation of the C3 convertase by properdin. The activity of properdin is to stabilise the C3bBb complex, retarding spontaneous and factor H-dependent dissociation. This stabilisation is ineffective in the fluid-phase, but seems to be more important in amplifying the process once it has already started on a suitable activating surface [5]. Increasing its activity (by increasing its affinity) may upset the balance in the fluid-phase, and thereby promote spontaneous C3 conversion. This should be particularly useful in combination with the other modifications described above.
  vi) Mutations that prevent the C3bBb from possessing C5 convertase activity. When used to deplete active C3 from the circulation an undesirable side-effect could be the generation of large amounts of anaphylactic peptides. The most potent of these is C5a, which is cleaved from C5 by some C3 convertase enzymes. This reaction probably depends on the affinity of the convertase for another molecule of C3b [11], and so may be subject to suppression by mutations to the C3 that remove this interaction.
  vii) Improved activity of the C3 convertase. The active site of the C3bBb C3 convertase enzyme resides in the Bb portion. The C3b component presumably functions to impose an active conformation on Bb and/or to bind and orientate the substrate to be acted upon by Bb. This is not known, but in either case there may be scope for enhancing the activity of the convertase through mutations in C3.

viii) Expression in a functional form. Wild-type C3 requires conversion to C3b before it can combine into a new C3 convertase complex. When used in vivo, a requirement for conversion to C3b (or C3i) would delay the action of the modified C3. It would therefore be desirable to either administer the protein in a form capable of immediate convertase formation, or to administer pre-formed convertase complexes. It is therefore advantageous to generate a functionally C3b-like reagent ex-vivo. This could be achieved in vitro (e.g. by proteolysis).

ix) Modifications to the native protein which serve to introduce new cleavage sites such that peptide regions required for factor B binding are retained but those required exclusively for factor H binding can be specifically removed. For example, sites can be introduced such that the C3b-like form of the modified C3 can be further cleaved into a form that still binds factor B but is less susceptible to inactivation by factors H and I.

x) Modifications in other regions which may affect the C3b interaction with factor B and/or factor H.

The invention is based on reversing the traditional approach by promoting C3 conversion to deplete C3 and thereby disable the system. An additional application of the invention is the potential to promote C3 conversion at a particular site, and thereby recruit the complement-dependent effector mechanisms to attack a specific target.

Therefore the ultimate effect will be to increase the amount of C3 conversion when the modified protein is administered into a physiological medium (e.g. blood) containing regulators of complement activation. This activity can then be used either to deplete that medium of native C3, or to localise the C3 conversion at a desired target.

The analogue of C3 whose C3b-fragment is resistant to the actions of factor I (e.g. the derivative described in example 1) would bind factor B, which would then be cleaved by factor D and eventually dissociate in an inactive form. In the absence of inactivation by factor I, the modified C3b would be able to repeatedly bind new molecules of factor B and thereby promote its inactivation. Therefore another potential application of modifications described in this invention would be the inactivation of the alternative pathway by consumption of factor B activity. An analogous approach could also be used to modify C4 to promote the consumption of C2, and thereby disable the classical pathway of complement activation.

The invention includes any other protease used in an analogous manner to the C3bBb enzyme which leads to cleavage of C3 to C3b, despite the presence of regulators of complement activation.

The invention also includes DNA sequences which code for a protein of the invention as well as DNA constructs comprising such DNA sequences.

"DNA sequences" include all other nucleic acid sequences which, by virtue of the degeneracy of genetic code, also code for the given amino acid sequence or which are substantially homologous to this sequence. These sequences are thus also included within the scope of the invention.

Nucleic acid sequences which are "substantially homologous" are also within the scope of the present invention. "Substantial homology" may be assessed either at the nucleic acid level or at the amino acid level. At the nucleic acid level, sequences having substantial homology may be regarded as those which hybridise to the nucleic acid sequences of the invention under stringent conditions (for example, at 35° to 65° C. in a salt solution of about 0.9M). At the amino acid level, a protein sequence may be regarded as substantially homologous to another protein sequence if a significant number of the constituent amino acids exhibit homology. At least 55%, 60%, 70%, 80%, 90%, 95% or even 99%, in increasing order of preference, of the amino acids may be homologous.

As discussed above the proteins of the invention can be used to achieve localised complement activation effects. One way of ensuring this is to conjugate the protein to a moiety which will bind at the desired target. Thus, in another aspect the invention provides a conjugate comprising a protein of the invention linked to a specific binding moiety, for example a specific binding protein. An example of such a protein would be an antibody or an antigen binding fragment thereof.

The proteins of the invention are intended to be administered to a subject to elicit a desired therapeutic effect. To that end therefore the invention also provides:

a) A protein of the invention for use in therapy;

b) The use of a protein or a conjugate of the invention in the manufacture of a medicament for use in depleting levels of complement pathway protein, and in particular for use in preventing rejection of foreign matter;

c) A pharmaceutical formulation comprising one or more proteins or conjugates of the invention together with one or more pharmaceutically acceptable carriers and/or excipients; and d) A method of reducing complement pathway protein in a mammal which comprises administering to the mammal a protein of the invention, preferably in the form of a pharmaceutical formulation.

Pharmaceutical formulations may be presented in unit dose forms containing a predetermined amount of active ingredient per dose. Such a unit may contain as a minimum, for example, 1 mg of active ingredient, and preferably 2–3 mg. The upper limit which such a unit dose can contain will depend on many factors such as the condition being treated, the route of administration and the age, weight and condition of the patient as well as economic considerations. As an example a unit dose form can contain as much as 10 mg or even 100 mg of active ingredient.

The proteins of the invention could be used in vivo to disable the complement system. Circumstances where this may be desirable include the following:

(a) In order to prevent complement-mediated destruction or damage to a transplant, particularly a xenograft (material transplanted from a different species of animal), and especially a discordant xenograft (where the donor and recipient species are discordantly related). The recipient would be decomplemented prior to the operation and maintained in this state until the transplant had either been accommodated or been replaced by a more compatible organ.

The initial treatment could be made within several days before transplantation. Additional decomplementation could be required at times of rejection crisis. The treatments may be accompanied by the use of antihistamine reagents to control the general inflammatory responses (e.g. vasodilation) likely to result from the generation of C3a and/or C5a.

Decomplementation may also be beneficial in the use of artificial organs or tissues (e.g. artificial kidney dialysis membranes) which activate the complement system. As described above, the protein may be given either as the unactivated form, a functionally C3b-like form or a pre-formed active C3 convertase (like C3bBb). These may be administered by any route whereby the active convertase will encounter the circulating C3 (e.g. intravenously, subcutaneously etc.).

Another alternative would be an ex vivo treatment, for example by transfusing the circulation through a matrix bearing the active convertase. This could have the advantage of allowing anaphylactic peptides (C3a and C5a) and other low molecular weight inflammatory mediators (e.g. histamine and nitric oxide) to be removed (e.g. by dialysis) prior to the decomplemented blood (or plasma) being returned to the patient.

(b) To prevent complement-mediated damage resulting from major surgery. The patient would be decomplemented, as above, preferably before the operation (but if necessary afterwards) and kept in this state until the danger of additional internal injury due to complement-dependent immune attack had diminished.

(c) To minimise complement-mediated damage resulting from non-surgical injury. In these cases the decomplementation must be performed after the initial injury, but the formulations and methods of administration are likely to be otherwise similar to those described above. This may be particularly useful when the recovery involves reperfusion of an ischemic tissue by the circulation (e.g. myocardial ischemia, frostbite, burns etc.).

(d) To minimise complement-mediated damage resulting from antibody-antigen interactions. Complement-mediated defensive responses are particularly undesirable in autoimmune diseases which may include glomerulonephritis, haemolytic anaemia, myasthenia gravis and type II collagen-induced arthritis. Disabling the complement system during severe episodes of disease may alleviate the condition.

(e) To make a specific pathogenic target more susceptible to complement-mediated immune mechanisms. In this approach, the aim is not to use the super-active C3 convertase to produce generalised depletion of C3, but instead to use the convertase locally to concentrate the C3 conversion at a desired target. The target may be a pathogenic organism, such as a bacteria, virus or other parasite, or a deleterious host cell or tissue, such as a tumour cell or a virally-infected cell. The C3 convertase could be localised to the target either by local administration (e.g. direct injection, possibly in a medium that retards its dispersion into the general circulation), or by combining with a targeting moiety, e.g. an antibody. Thus the modified protein could be linked to a specific immunoglobulin either by chemical cross-linking of the proteins, or by joining the DNA coding sequences and expressing (and purifying) the fusion protein (e.g. in the case of IgG, either the heavy or the light chain could be attached to C3 and co-expressed with C3, or both chains could be combined within one complete fusion polypeptide), or by incorporation of specific coding sequences (eg. for "leucine zipper"-like domains) to the DNA of both fusion partners (eg. modified C3 and specific antibody) such that the expressed products, when mixed together, self-associate to form stable conjugates. The fusion protein could then be administered locally or into the general circulation.

Liposomes (bearing the antibody on the surface with the modified protein either on the surface or inside the liposome) and/or virions (e.g. engineered to express the proteins on their surface) could also be used for co-delivery of antibody and modified protein. This strategy could be used directly, alone or in combination with other treatments, at any stage in the disease process. It may be particularly appropriate for use in eliminating any cancerous cells left in the circulation after surgical removal of a tumour. The antibody-modified protein conjugates could also be used ex vivo to eliminate pathogenic tissue. For example to kill leukaemic cells from an extracted bone-marrow and then returning the remaining healthy cells to the patient.

Alternatively lymphocytes that do not match the MHC types of the recipient could be eliminated from a bone marrow prior to transplantation. Also the modified protein could be linked to an antigen, and this combination could be used, either in vivo or ex vivo, to attack lymphocytes of undesirable reactivities (e.g. against transplant or self tissue).

The same technology would be applicable to treating other species, using either a human modified protein derivative, or a similar analogue tailor-made for that species.

Preferred features of each aspect of the invention are as for each each other aspect mutatis mutandis.

The invention will now be described by way of the following examples, which should not be construed as in any way limiting the invention. The examples refer to the accompanying drawings in which:

BRIEF DESCRIPTION OF THE DRAWINGS

FIG. 1 shows the predicted protein sequence of human C3 as encoded in PC3; (using the standard one letter amino acid code)

FIG. 2 shows the cDNA sequence in PC3; (using the standard one letter deoxynucleotide code for the sense strand, written 5'-3').

Figure 3:
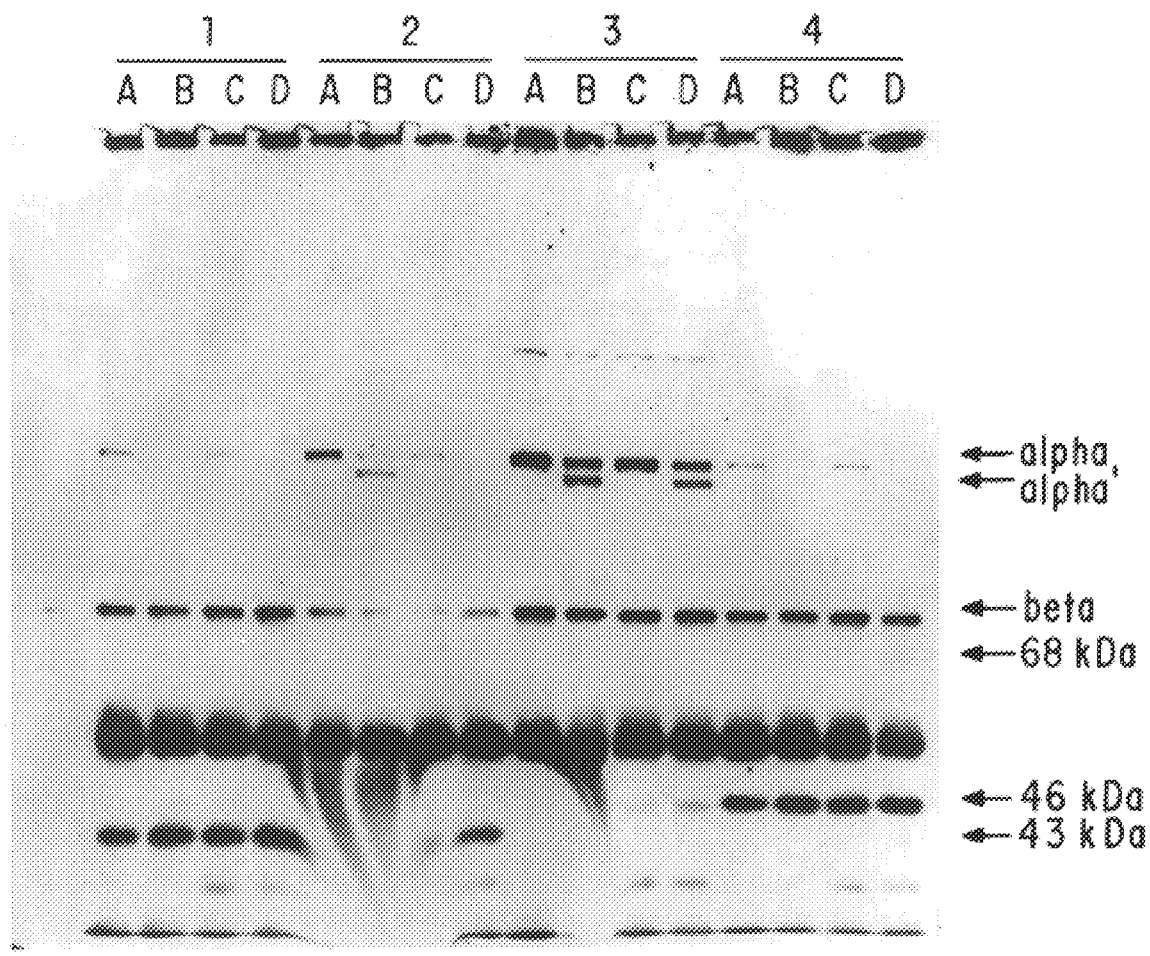
FIG. 3 shows a visualisation of modified proteins of the invention.
Figure 4:
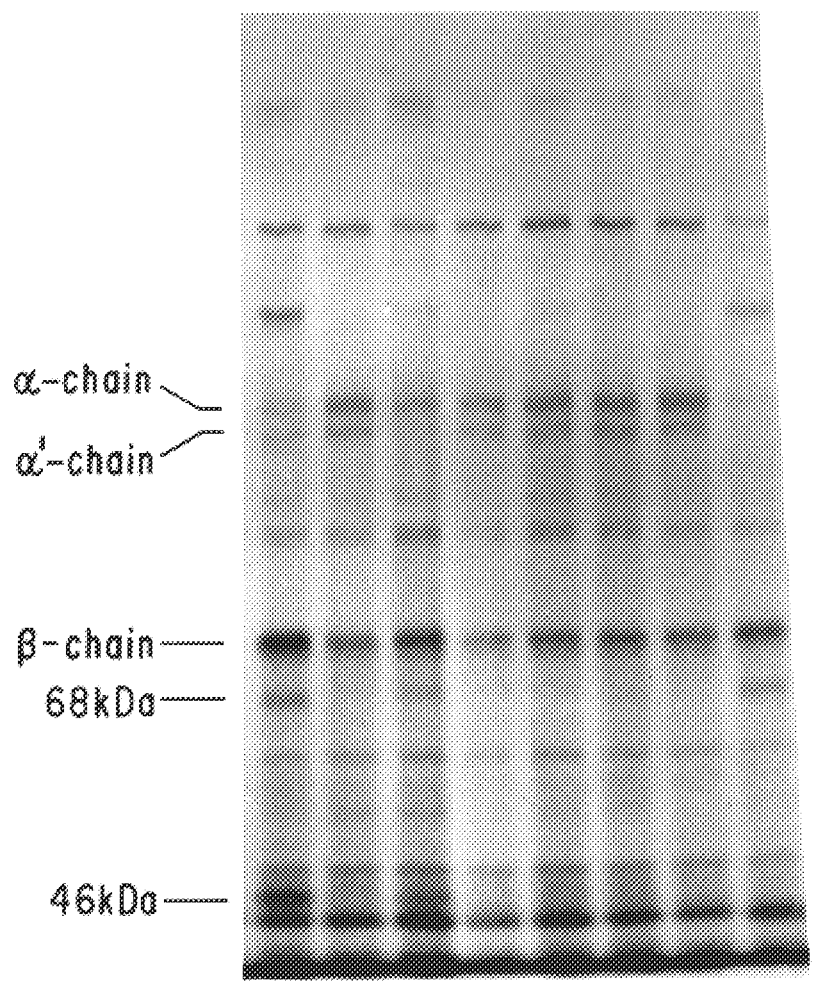
FIG. 4 shows the effect of various mutations to human C3 which replace Arg 1303 or Arg 1320 on factor I-medicated cleavage at these sites. N.B.
  1. [35S]-biosynthetically labelled samples.
  2. Reactions performed at normal ionic strength.
  3. Immunoprecipitated with anti-C3.
  4. SDS-PAGE under reducing conditions.
  5. Autoradiography.

This is a photograph of a Western Blot developed from a 7.5% polyacrylamide SDS-PAGE gel (reducing conditions), after electrophoretic transfer onto nitrocellulose, probing with a sheep anti-human C3 antibody, and development with horse-radish-peroxidase-coupled anti-sheep Immunoglobulin antibody and Enhance ChemiLuminescence (method and detection reagents from Amersham, U.K.) recorded on X-ray film. The cleavage reactions and detection procedure were performed as described in Example 4 with reference to the results shown in FIG. 3.

Key:
  Tracks 1–4: wild-type C3 (expressed in COS cells)
  Tracks 5–8: Mutant C3 (residues 752–754 changed to Gly-Ser-Gly and residues 758–760 also being changed to Gly-Ser-Gly) (expressed in COS cells)

Figure 7:
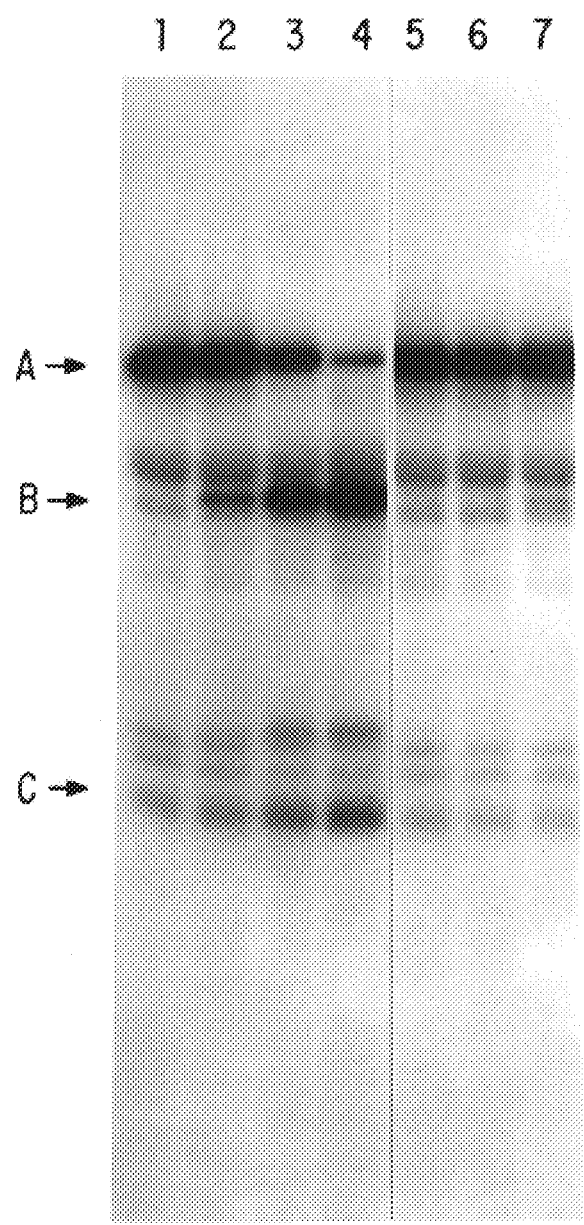

Tracks 1,5: no addition
Tracks 2,6: +CVFBb
Tracks 3,7: +factors H+I
Tracks 4,8: +CVFBb+factors H+I The bands indicated by arrows are:
A: C3 alpha-chain
B: C3 alpha'-chain
C: C3 beta chain
D: 68 kDa cleavage product of C3 alpha'-chain
E: IgG heavy chain FIG. 7 shows an analysis of the cleavage of radiolabelled factor B by factor D, in the presence of wild-type and mutant C3's (C3i's)

A photograph of the autoradiograph of the SDS-PAGE gel is shown. All samples contained factor D and $^{125}$I-labelled factor B, and were incubated for 3 hours at 37° C.

The samples in the numbered tracks also included:
1. Buffer alone
2. 1/125 wild-type C3
3. 1/25 wild-type C3
4. 1/5 wild-type C3
    1/25 mutant C3 (residues 1427 Gln, 1431 Asp and 1433 Gln)
5. 1/5 mutant C3
7. undiluted mutant C3

The bands indicated by arrows are:
A. Uncleaved $^{125}$I-labelled factor B (93 kDa)
B. 60 kDa cleavage product ("Bb")
C. 33 kDa cleavage product ("Ba")

Figure 8:
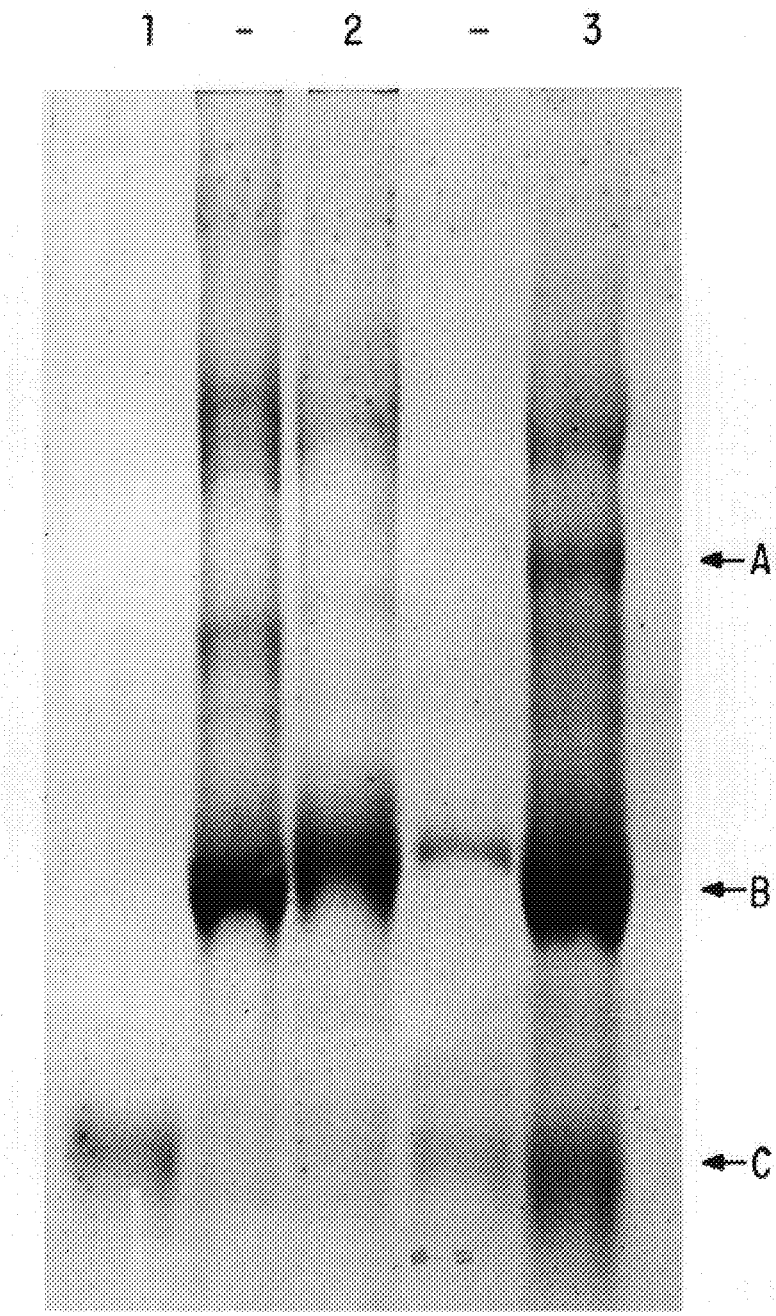

FIG. 8 shows an SDS-PAGE study illustrating the formation of a conjugate between C3i and IgG.

This is a Coomassie stain of a 4% acrylamide SDS-PAGE gel run under non-reducing conditions. The numbered tracks contain samples of:
1. PDP-IgG
2. C3i
3. PDP-IgG+C3i reaction mixture Indicated by arrows are:
A. Probably C3i-IgG conjugate (350 kDa)
B. C3i (200 kDa)
C. IgG (150 kDa)

Figure 9:
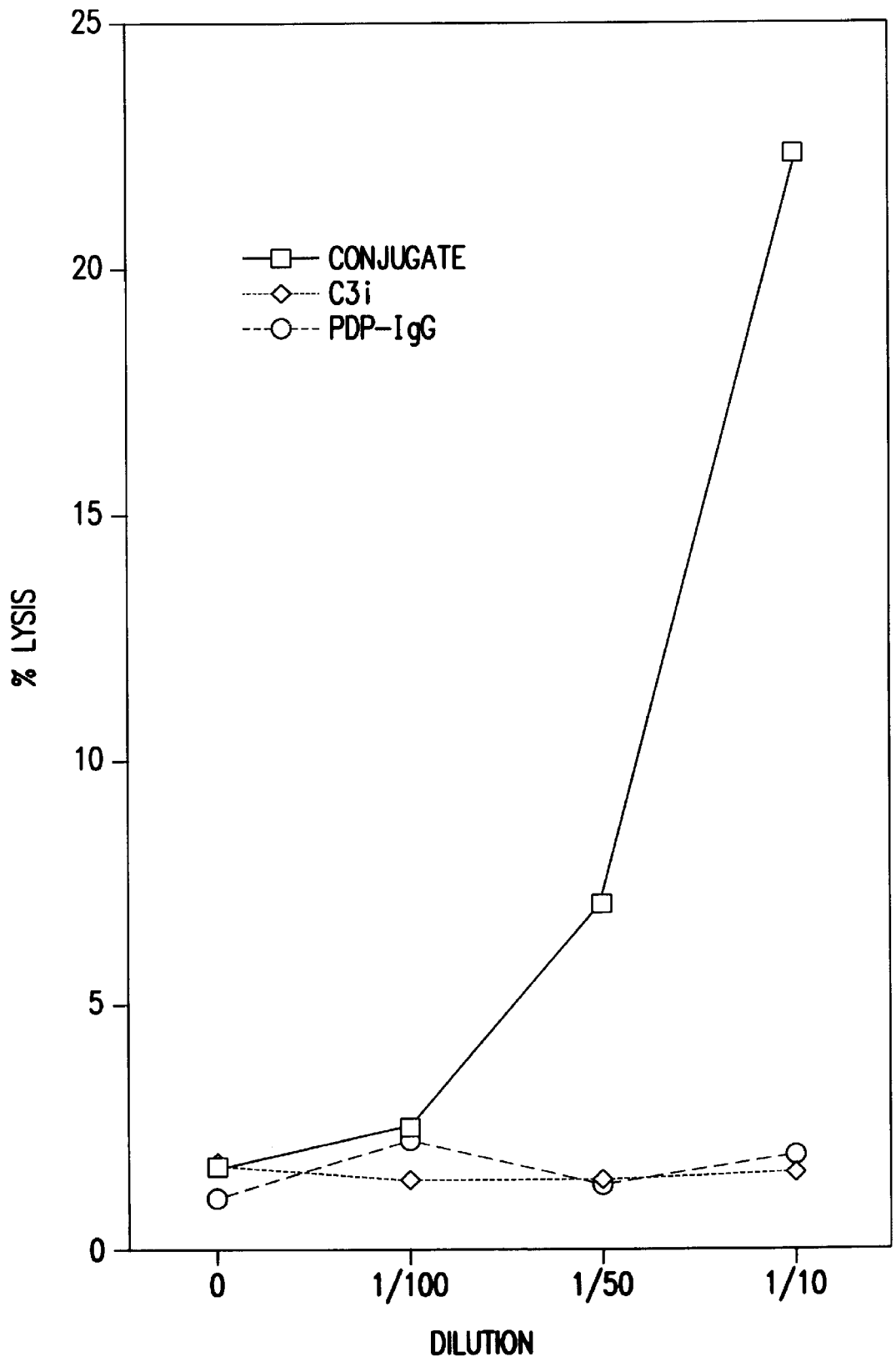

FIG. 9 demonstrates that conjugate targets C3 convertase activity against sheep erythrocytes. (This graph shows the % lysed sheep erythrocytes after coating with dilutions of either the C3i-IgG conjugate, PDP-IgG or C3i followed by washing, generation of C3 convertases with properdin and factors B and D, and finally development of lysis by NGPS in CFD/EDTA, as described in the methods. Only the conjugate produces lysis, and this lysis is dose dependent.)

DETAILED DESCRIPTION

The following standard methods and definitions are applicable to all the examples.

All complement components referred to are of human origin, unless otherwise specified, using standard terminology for all proteins and their derived fragments (e.g. as contained in reference [15]). In addition the term "C3i" refers to any molecular form of C3 without an intact thiolester bond, but retaining the C3a polypeptide on the alpha chain.

The human C3 cDNA and coding sequence are numbered as shown in FIG. 2, using the numbering used in the EMBL nucleotide data base (derived from reference [2]). The sequence shown is that of our construct ('PC3'), which lacks the first 11 nucleotides of the 5' untranslated region reported in reference [2], and hence the first base is numbered 12. The putative initiation codon is nucleotides number 61–63, the codon for the amino-terminal serine residue of the beta-chain is nucleotides 127–129, and the codon for the amino-terminal serine residue of the alpha-chain is nucleotides 2074–2076.

The protein sequence is numbered according to the precursor sequence as shown in FIG. 1, which is a predicted translation of the DNA sequence in Appendix 1 (amino acids 1–22 are expected to comprise a signal sequence that is removed during biosynthesis, and amino acids 668–671 are expected to be removed when the precursor is cleaved into the alpha and beta chains).

The following abbreviations have the following meanings;

CVBF cobra venom factor; ELISA, Enzyme-linked immunoadsorbant assay; *E. coli, Escherichia coli*; kb, kilobase; HSV-1, herpes simplex virus type 1; PBS, phosphate-buffered saline. COS-1 is a cell line derived from monkey kidney cells. The following are restriction endonucleases: AflII, DraI, DraIII, EcoRI, EcoRV, HindIII, NaeI, NheI, XbaI.

Standard methods

Methods for standard molecular biological procedures such as plasmid isolations, agarose gel electrophoresis, and DNA ligations can be found in reference [21]. Double stranded DNA was sequenced using the 'Sequenase version 2.0' kit supplied by 'United States Biochemicals'. C3 expression was measured by an ELISA assay using plastic plates pre-coated with affinity-purified polyclonal sheep anti-human C3 to which samples of culture supernatant were added. Bound C3 was detected with a monoclonal rat antibody to C3 conjugated to alkaline phosphatase, and the chromogenic substrate, p-nitrophenol phosphate. Assays were calibrated with purified human plasma C3.

Methods for purification of complement proteins and CVF, and for the preparation of affinity purified anti-C3 antibodies used in the analysis can be found in reference [28]. Equivalent reagents can also be purchased from Sigma chemical company LTD.

C3 cDNA coding sequence

Our C3 cDNA coding sequence was constructed from two segments isolated from a random-primed human liver cDNA library carried in the vector pGEM4 (Promega). Five oligodeoxynucleotides, corresponding to known segments in the human C3 coding sequence, were radiolabeled with T4 polynucleotide kinase and [γ-32P]ATP and used to probe filter transfers of the library from agarose plates. Two clones containing inserts of approximately 4 kb were isolated. Restriction endonuclease digestion, hybridisation to specific oligodeoxynucleotide probes and partial sequence analysis demonstrated that one of these ('A13') included the 5'-end of the 5.1 kb message, whereas the other ('B44') extended to the 3'-end.

These inserts therefore overlapped by approximately 3 kb, including a unique EcoRI restriction enzyme site. The incomplete 5' section of A13 was cut out with EcoRI and NheI, and replaced with the complete segment isolated from B44 by digestion with EcoRI and XbaI. Both pieces were purified by gel electrophoresis in low-melting point agarose before ligating together with T4 DNA ligase to produce a vector ('PGC3') containing 5.1 kb of DNA encoding the entire C3 precursor protein.

Linker sequences 5' to the C3 coding region contained two ATG's which are potential false translation start sites. These were therefore removed by gapped-plasmid mutagenesis, as described in the method of example 1, using an oligodeoxynucleotide PL-ATC-3 (tagggagacc ggaagcttgc cctctccctc tgtccctctg t) that deleted approximately 50 base pairs of linker/adaptor DNA, without altering the C3 coding sequence. This mutated vector, 7.7 kb containing 5.1 kb of C3 cDNA sequence plus 2.6 kb of sequence from the PGEM4 vector (Promega) is referred to as PC3.

The C3 coding region of the PGC3 plasmid was completely sequenced and revealed only four differences from a previously published human C3 ("S" allele) cDNA sequence [2].

(i) the changes C2481→G, and C2805→T do not alter the coding;

(ii) T1001→C encodes the previously described HAV 4-1-(Leucine314→Proline) polymorphic form [20]; and (iii) G2716→A encodes Valine886→Isoleucine, that has not been previously reported in human C3, although Ile is found in this position in mouse and rat C3.

Our sequence includes start and stop codons, with a complete signal sequence and should, therefore, encode functional C3.

Levels of up to 1.7 μg/ml expressed wild type C3 in culture supernatants of COS-1 cells (transfected using lipofectamine and the pcDNA3 (Invitrogen) expression vector) have been detected by ELISA. No detectable C3 was produced by cells transfected with pcDNA3 vector alone. Furthermore, analysis of the expressed product by cleavage reactions followed by immunoprecipitation, SDS-PAGE and immunoblotting demonstrated that:

(i) the primary translation product had been correctly processed into the mature two-chain form;

(ii) this product was, like native C3, cleavable to C3b by C3 convertase (CVFBb); and (iii) the expressed protein was, like native C3, not cleavable by factor H plus I, but became cleavable after conversion to C3b by C3 convertase enzyme. This confirms that our starting plasmid can be translated into functional C3.

For an alternative description of a construction and expression of a C3 coding sequence see reference [25].

EXAMPLE 1

Production of C3 that has the arginine residues at both factor I cleavage sites (amino acid positions 1303 and 1320) converted to glutamine residues to prevent cleavage of the C3b fragment by factor I.

a) Mutagenesis

Mutagenic oligodeoxynucleotides used were QRI1 (caactgcccagccaaagctccaagatcacc), QRI2 (gccagcctcctgcaatcagaagagaccaag), and AFL4149 (taataaattcgaccttaaggtcaccataaaac), as well as the corresponding antisense oligodeoxynucleotides QRI1n (ggtgatcttggagctttggctgggcagttg), QRI2n (cttggtctcttctgattgcaggaggctggc) and AFL4149n (gttttatggtgaccttaaggtcgaatttata).

QRI1 and QRI1n specify the replacement of arginine for glutamine at the factor I cleavage site at amino acid residue 1303 in the C3 precursor sequence (by changing G3968C3969 to AA in the cDNA sequence), and QRI2 and QRI2n effect the same substitution at the factor cleavage site at amino acid residue 1320 (by changing nucleotide p4019 to A).

AFL4149 and AFL4149n introduce a cleavage site for the restriction endonuclease AflII at position 4149 in the cDNA sequence (by changing C4149 to T) without altering the encoded amino acid sequence. These two primers were used as markers, allowing successful mutagenesis to be identified on the basis of cleavage of the DNA product by AflII.

Mutagenesis was effected using the 'gapped plasmid' method. A batch of PGC3 ('UPGC3'), enriched in uridine in place of thymidine, was prepared by growth in E. Coli strain CJ236 in the presence of 0.25 μg/ml uridine. This plasmid was digested with SmaI and the 7.2 kb product ('US1') agarose gel purified to remove a 0.5 kb fragment from the C3 sequence (residues 1463–1947). The other component of the gapped plasmid ('DN2') was prepared by digesting PGC3 with DraIII plus NaeI and purifying the 5.1 kb piece twice by agarose gel electrophoresis. 200 ng DN2 was mixed with approximately 500 ng US1 in 50 μl H2O, heated to 100° C. and cooled slowly to below 50° C., before adding 20 μl to 25 μl of 2XT7 buffer (100 mM Tris/HCl/pH 7.4/14 mM MgCl2, 100 mM NaCl, 2 mM dithiothreitol, and 1 mM each of ATP, DATP, dCTP, dTTP and dGTP) plus 10 nmol of each 5'-phosphorylated mutagenic primer (one reaction used QRI1, QRI2 plus AFL4149, another reaction used QRI1n, QRI2n plus AFL4149n). The mixtures were reheated to 70° C. for 5 min and cooled slowly (over 30–60 min) to 20° C. At 0° C., 10 units of T7 DNA polymerase plus 80 units T4 DNA ligase are added. The mixture (total volume 50 μl) was incubated first at 0° C., for 5 min, then at room temperature for 5 min, and finally at 37° C. for 3 hours. 1 μl of each mixture was used to transform 100 μl supercompetent XL1 E. Coli (Stratagene) according to the manufacturer's instructions.

Ampicillin resistant colonies were screened for AflII cleavage, and successful mutants were grown up in 100 ml cultures from which the plasmids were isolated and sequenced (using a sequencing primer C3pa-3876, cttcatgtgtgttccaagcct, matching nucleotides 3876–3895 of C3 cDNA) to characterise mutations at the factor I cleavage sites.

For an alternative protocol for "gapped plasmid" mutagenesis see references [26,27].

b) Transfer of mutant DNA to eukaryotic expression vector

The C3 coding fragments from mutant plasmids were excised is by double digestion with HindIII and NaeI. DraI was also included to incapacitate the residual plasmid. The C3 coding sequence was agarose gel purified and ligated into pcDNA3 vector (Invitrogen) that had been linearised with HindIII and EcoRV enzymes and dephosphorylated with calf intestinal phosphorylase. Ligation mixtures were used to transform supercompetent XL1 E. coli, which were then plated onto culture plates containing ampicillin.

A random selection (three or four) of ampicillin resistant colonies were grown up in 2–3 ml cultures and small scale isolation of the plasmid DNA. The plasmids containing the correct insert were identified by digestion of the plasmid DNA with restriction endonucleases EcoRI, HindIII and AflII. The corresponding colonies grown up in 100 ml cultures and the plasmids purified by the standard procedure. These mutants were originally constructed from PGC3 and so retained the two ATG's 5' to the coding region. This region (plus the 5' 3 kb of the C3 coding sequence) was therefore excised with HindIII plus EcoRI and replaced by ligation of the same segment cut out of PC3. These reconstructed vectors were prepared by the standard procedure and used for transfection of COS cells.

c) Expression of wild-type and mutant C3's

Mutants and wild-type C3 were transiently expressed from plasmids transfected into COS-1 cells using lipofectamine® (GIBCO) according to the manufacturer's instructions. Typically, 1–1.5×10$^5$ cells per well of a standard 6 well culture plate were transfected with 2–4 μg of plasmid using 9 μl of lipofectamine reagent. Supernatants were assayed for C3 secretion, and typical yields of 0.3–1.7 μg per ml supernatant were obtained 3–6 days after transfection.

Results a) Generation of mutants

The following mutants, named according to the mutagenic oligodeoxynucleotide sequences that have been incorporated, have so far been isolated:

(i) 3 mutants with both QRI1 and QRI2 mutations plus AFL4149: C3M-26, C3M-58 and C3M-61;

(ii) 1 mutant with QRI1 and QRI2 but without AFL4149: C3M-8; and (iii) 1 mutant with QRI2 and AFL4149, but without QRI1: C3M-51 (used in example 3)

b) Validation that functional effects were due to the mutations specifically introduced at the factor I cleavage sites Sequencing has confirmed the absence of other alterations in 178–350 bases around the mutated region of each mutant. The sequence of one mutant produced by this procedure, C3M-51 (see example 3), has been analysed throughout the entire 'gap' (bases 2463–5067) used fin mutagenesis, and no other deviations from the wild-type sequence were found.

Furthermore, representative sequencing of a total of 2922 bases from all mutants have not revealed any single point mutations that could have been caused by polymerase-mediated errors. The expressed mutants all displayed the two-chain structure and cleavage by C3 convertases characteristic of native C3. In summary, the mutants used are unlikely to contain any unwanted changes although they have not been completely re-sequenced.

EXAMPLE 2

Production of C3 that has the arginine residue at one factor I cleavage site (amino acid position 1303) converted to a glutamine residue The procedure of Example 1 was followed except that only mutagenic oligodeoxynucleotides AFL4149 plus QRI1 or AFL4149n plus QRI1n (i.e. no QRI2 or QRI2n), were used in mutagenesis.

Results a) Mutants obtained 2 mutants with QRI1 and AFL4149 but without QRI2 were isolated:-C3M-I23,27. The mutant C3M-I23 was expressed, as described in Example 1.

This protein was cleavable by CVFBb. The C3b-like product was relatively (compared to the wild-type) resistant to cleavage at position 1303 by factors I and H, but could still be cleaved at position 1320. This C3b derivative is therefore partially resistant to factor I.

EXAMPLE 3

Production of C3 that has the arginine residue at one factor I cleavage site (amino acid position 1320) converted to a glutamine residue The procedure of Example 1 was followed except that only mutagenic oligodeoxynucleotides AFL4149 plus QRI2 or AFL4149n plus QRI2n (i.e. no QRI1 or QRI1n), were used in mutagenesis. In addition, the method used in example 1 also yielded one mutant with QRI2 and AFL4149, but without QRI1.

Results a) Mutants obtained 3 mutants with QRI2 and AFL4149 but without QRI1 were isolated:-C3M-51, C3M-Q2, C3M-Q13. The mutant C3M-51 was expressed, as described in Example 1. This protein was cleavable by CVFBb. The C3b-like product was not readily cleaved at position 1320 by factors I and H, but it could still be cleaved at position 1303. This C3b derivative is therefore partially resistant to factor I.

EXAMPLE 4

Analysis of the functional effects of mutations.

Supernatants (100–400 μl) from transfected COS cells were incubated at 37° C. for 2 h with:

COS cells were transfected with pcDNA3 carrying inserts of:

1) the unmutated C3 sequence;

2) mutant C3M-I23 (encoding $Arg^{1303}$→Gln);

3) mutant C3M-26 (encoding $Arg^{1303}$→Gln, $Arg^{1320}$→Gln); and 4) mutant C3M-51 (encoding $Arg^{1320}$→Gln).

200 μl of the culture supernatants, taken 3 days after transfection, were pretreated with 2 mM phenylmethanesulphonyl fluoride (0° C., 15 min) and then incubated at 37° C. for 2 hours with the following:

A) no addition;

B) preformed C3 convertase, CVFBb (10 μl from 200 μl containing 6.6 μg CVF, 100 μg factor B and 1.4 μg factor D in phosphate-buffered saline (PBS) containing 10 mM $MgCl_2$, preincubated at 37° C., 15 mins);

C) factors H (5 μg) and I (1 μg); and

D) CVFBb plus factors H and I.

These were then immunoprecipitated by adding 0.6 μg affinity-purified sheep anti-human C3 immunoglobulin at room temperature and after 1 hour adding 20 μl a 5% suspension of washed formalin-fixed Group C Streptococcus sp. cells (protein G) (Sigma). After 45 min at room temperature the particles were washed once in PBS, 5 mM $NaN_3$, and once in 20 mM Tris/HCl, 137 mM NaCl, 0.1% (v/v) Tween 20, pH 7.6 before eluting in 1% SDS/2% 2-mercaptoethanol (90°–100° C., 5 min). These eluates were separated by SDS-PAGE, electroblotted onto nitrocellulose and the C3 bands detected by probing with affinity-purified sheep anti-human C3 immunoglobulin followed by horse radish peroxidase-coupled donkey anti-sheep immunoglobulin (Sigma) and detection using the "Enhanced Chemiluminescence" substrates supplied by Amersham. A photograph of a 2 minute exposure to X-ray film is shown. The visible C3-derived bands are indicated by labelled arrows, and the individual samples (1–4, A–D) are those just described. (The prominent band of about 50 kDa (between the 46 and 68 kDa bands) present in all samples is the heavy chain of the IgG used in the immunoprecipitation and detected by the horse radish peroxidase-coupled donkey anti-sheep immunoglobulin.).

Results (see FIG. 3)

1. All the untreated samples (1-A, 2-A, 3-A, 4-A) contain bands of the correct migration for alpha and beta chains of C3, indicating that all the mutants are expressed, and post-translationally processed correctly. The presence of 43 or 46 kDa bands in these samples indicates the presence of some factor H+ factor I-like activity in the culture medium. Spontaneous hydrolysis of C3 during the 3 day biosynthetic period produces C3i which is cleaved by this activity. In the unmutated C3 this generates bands of 43 kDa and 75 kDa (the 75 kDa band is invisible because (i) it is hidden by the 75 kDa beta chain, and (ii) the antibody used to develop the western blot has very little activity towards this portion of the C3 alpha chain:—its presence was subsequently confirmed by reprobing with a rat monoclonal antibody, "Clone-3", that is specific for this region). The addition of factors H and I without CVFBb (1-C, 2-C, 3-C, 4-C), did not cleave the remaining C3 indicating that this represented active C3 (thiolester intact).

2. The unmutated C3 (1) is cleaved by CVFBb and the C3b product is further cleaved by endogenous enzymes in 1-B or added factors H and I in 1-D. The 43 kDa band indicates cleavage at $Arg^{1320}$, and the 68 kDa band (visible in longer exposures) indicates cleavage at $Arg^{1303}$.

3. The mutant C3M-I23 ($Arg^{1303} \rightarrow Gln$) was cleavable by CVFBb and the product was relatively resistant to endogenous factor H and I-like activity (2-B), with distinct amounts of alpha' chain (C3b) persisting, but was still cleavable when extra factor H and I were added (2-D). The 43 kDa product indicates cleavage at $Arg^{1320}$, (a faint band at 71 kDa representing the other fragment of the alpha' chain could be seen in longer exposures) but no 68 kDa band was present, showing that this mutant is resistant to cleavage at the mutated $Gln^{1303}$.

4. The mutant C3M-26 ($Arg^{1303} \rightarrow Gln, Arg^{1320} \rightarrow Gln$) was cleavable by CVFBb and the C3b-like product (alpha') was resistant to endogenous factor H and I-like activity (3-B). It was also very resistant to the additional factors H and I (3-D) in comparison with the unmutated C3 (1) and other mutants (2 and 4). There was a small amount of 46 kDa product indicating some cleavage at the mutated $Gln^{1303}$ (the accompanying 68 kDa fragment was also visible on longer exposures). There was little or no detectable 43 kDa that would correspond to any cleavage at $Gln^{1320}$. Therefore the Arg→Gln mutation at position 1303 is less effective than that at position 1320 at preventing cleavage by factor I. (This slow residual cleavage might also be occurring in the mutant C3M-I23 ($Arg^{1303} \rightarrow Gln$), but the 46 kDa intermediate is probably being rapidly processed to 43 kDa by further cleavage at the unmutated $Arg^{1320}$.)

5. The mutant C3M-51 ($Arg^{1320} \rightarrow Gln$) was cleavable by CVFBb and the product was cleaved by endogenous factor H and I-like activity (4-B), and by additional factor H and I (4-D). The 46 kDa product (and faint 68 kDa band) indicates cleavage at $Arg^{1303}$. However, the absence of a 43 kDa band indicates that it is not cleaved at the mutated $Gln^{1320}$.

EXAMPLE 5

Comparison of various amino acid substitutions at position 1303

1. Introduction

The previous examples described mutations of arg 1303 and arg 1320 to glutamine residues. Both mutations imparted resistance to cleavage at those positions by factor I. However, there was a small but detectable degree of cleavage at gln 1303. Therefore a number of other amino acid substitutions at this position have been made and tested. Cleavage occurs, in decreasing order of efficacy when residue 1303 is: Arg>Tyr>[Cys or Trp]>Gln>[Glu or Gly]. These results are unexpected because (i) all known naturally occurring human factor I-mediated cleavages occur C-terminal to arginine residues, so it would have been deduced that the enzyme had a requirement for arginine; and (ii) if it did cleave at other residues one would predict that they would have to be electrostatically similar to arg, i.e. a basic residue Wlys or his), (e.g. trypsin selectively cleaves C-terminal to arg, lys or his), so one could no: have predicted cleavage of the tyrosine substitution.

Therefore substitution of arg 1303 with glycine or glutamic acid is preferred for the purpose of creating a derivative of C3 resistant to inactivation by factor I.

2. Methods 2.1 Mutagenesis: the degenerate mutagenic primer used was:

caactgcccagc(gt)(ag)(cg)agctccaagatcacc (letters in brackets indicate mixture of bases at that position). Mutants were constructed either by the gapped-plasmid method (as described in the earlier examples), or by the "megaprimer method" (V. Picard et al, *Nuc Acid Res* 22:2587–91, (1994)), in which the upstream primer was caccaggaactgaatctagatatgtccctc and the downstream primer was gttttatggtgaccttaaggtcgaatttatta. All mutations were performed on templates in which the C3-encoding DNA had already been mutated such that amino acid residue 1320 was glutamine, and a restriction site for AflII had been introduced at position 4149 (as described in the earlier examples) and were confirmed by DNA sequencing.

2.2 Expression: mutants were expressed in COS cells using the pcDNA3 vector as described in the earlier examples, biosynthetically labelled with [$^{35}$S]methionine in serum-free medium.

2.3 Assay: the supernatants were treated with CVFBb (formed by reaction of CVF with factors B and D in magnesium-containing buffer) and factors H and I followed by immunoprecipitation with anti-C3 and separation by SDS-polyacrylamide gel electrophoresis performed under reducing conditions (as described in the earlier examples). The gel was fixed, treated with Amersham "Amplify" reagent, dried and exposed to autoradiography film to yield the result shown in the figure.

3. Results

Factor I-mediated cleavage at position 1303 (site 1) without cleavage at 1320 (site 2) (where this has been mutated to glutamine) produces bands of 46 and 68 kDa. It can be seen that cleavage occurs in the order: arg(R)>tyr (Y)>cys(C) and trp(W)>gln(Q)>gly(G) and glu(E). The wild-type (arginine at both positions) is cleaved at both positions to produce fragments of 43 (too small to be visible on this gel) and 68 kDa.

4. Figure

The results are shown in FIG. 4. The residues at site 1 (position 1303) and site 2 (1320) are indicated above the respective tracks.

EXAMPLE 6

Demonstration of enhanced resistance to inactivation by factors I and H after mutation of arg 1303 to gln 1. Introduction The earlier examples demonstrated that conversion of either arg 1303 or arg 1320 to glutamine made that site resistant to cleavage by factor I. Mutation of both sites makes a molecule that is resistant to cleavage at either site. Here, we further demonstrate that mutation of arg 1303 to gin alone (without alteration to arg 1320) results in a considerable resistance, compared to the wild-type, to functional inactivation by factors I and H.

2. Method 2.1 Expression: The preparation of the arg 1303→gln mutation was described in an earlier example. This was transfected into CHO (a common laboratory cell line derived from chinese hamster ovary cells) by the calcium phosphate method, and stable transfectants selected on the basis of resistance to G418 ("Geneticin" available from Sigma). Cell culture supernatants were collected, and the expressed C3 was partially purified by sodium sulphate precipitation (10–20% (w/v) fraction), and ion-exchange chromatography on Q-sepharose and mono-Q sepharose (A W Dodds *Methods Enzymnol* 223: 46 (1993)).

2.2 Assay: Sheep erythrocytes were coated with SO16 monoclonal antibody (R A Harrison and P J Lachmann *Handbook of Experimental Immunology* 4th Edition chpt. 39 (1986)) and 4.4 ml of a 5% (v/v) suspension was then incubated with approximately 10 μg C2, 24 μg C4 and 1 μg C1 (purified human components) for 10 min at 37° C. in CFD (R A Harrison and P J Lachman supra). 0.8 ml of this mixture was then incubated for 105 min with 0.25 ml containing the semi-purified mutant or wild-type C3 and EDTA to a final concentration of 12.5 mM. The cells were then washed in CFD and used in CFD containing 0.1% (w/v) gelatin (CFD-gel). Radioligand binding with [$^{125}$I]-labelled clone 4 monoclonal anti-C3 antibody was used to confirm that similar amounts of wild-type or mutant C3b were deposited.

For the assay, 40 μl of a 5% suspension of cells was diluted in 250 μl CFD-gel and 50 μl aliquots were incubated with 50 μl CFD-gel containing dilutions of factors I and H to final concentrations of 100, 10, 1 and 0 μg/ml each, at 37° C. for 30 min. 0.9 ml of CFD was then added, the cells pelletted by centrifugation and washed twice more with 1 ml of CFD each time. The cells were then resuspended in 100 μl CFD-gel containing 100 μg/ml factor B, 100 μg/ml properdin, 1 μg/ml factor D and 0.3 mM $NiCl_2$. After 10 minutes at 37° C., 0.9 ml of CFD containing 10 mM EDTA and 2% (v/v) normal guinea-pig serum. After a further 30 min at 37° C., unlysed cells were pelletted by centrifugation, and the degree of lysis determined by measuring the absorbance of the supernatant at 412 nm. The absorbance equivalent to 100% lysis was determined from an aliquot of cells lysed in water, and hence the percentage lysis was calculated.

This assay measures the ability of deposited C3b to form a functional C3bBbP convertase. Conversion to iC3b prevents convertase formation and subsequent lysis in serum/EDTA.

3. Results

The result shown in the figure indicates that more than ten times as much factor I and factor H are required to abrogate the hemolytic activity of the arg 1303→gln mutant, when compared to the wild-type. This mutation is therefore advantageous for the creation of a derivative of C3 whose C3b product is resistant to inactivation by factors H and I. The effect could either be due to the greater resistance to cleavage at position 1303 (when arg is mutated to gln), or to greater resistance to cleavage at position 1320 when cleavage can first take place at position 1303.

4. Figure

Figure 5:
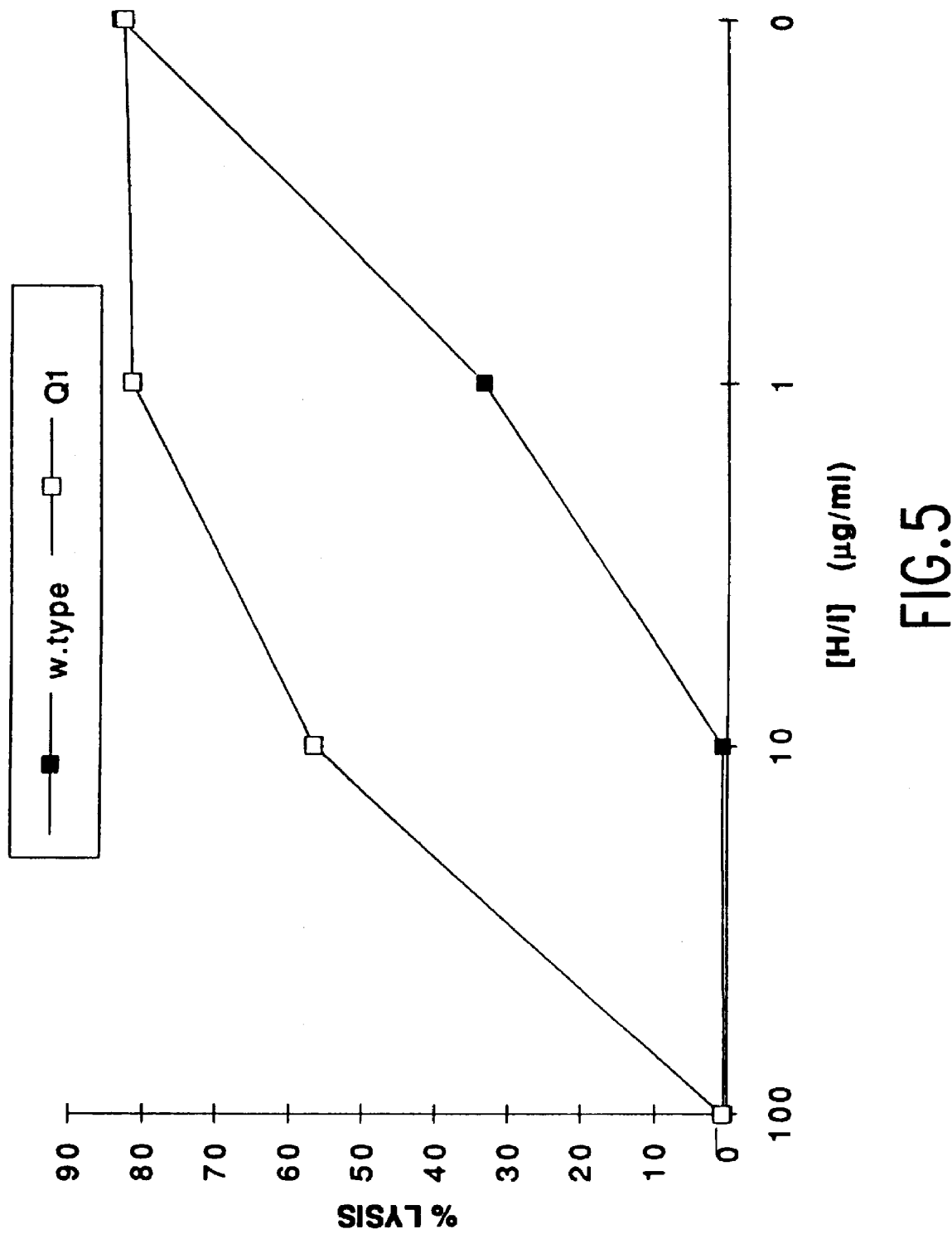
FIG. 5 shows enhanced resistance of human C3 incorporating the Arg 1303→Gln 1303 mutation to inactivation by factors I and H.

The results are shown in FIG. 5. The x-axis indicates the concentration of factors H and I. Q1 represents the arg 1303→gln mutation. % lysis is measured as described in the methods.

Discussion

The essential features of Human C3, with respect to modified variants described herein are as follows:

(i) The molecule has a functionally C3b-like derivative in that it can combine with functionally active human factor B, which can then be cleaved by human factor D to form an enzyme capable of cleaving human C3.

(ii) The amino acid sequences of derivatives are more homologous to C3 from humans than to C3 from any other species for which a sequence is presently known, or to any other presently known protein sequence. Structural features of C3 present in wild-type protein, but not necessarily in modified derivatives, include the following:

(a) The DNA coding sequence and translated protein sequence for the variant of human C3 used in the examples of the invention described herein are given in FIGS. 2 and 1 respectively. This protein sequence differs from the published sequence [2] at just two amino acids (details are given in the examples). It is assumed that many more variations are compatible with C3 function, even though most will not be present in the population.

(b) The primary translation product is proteolytically processed into two disulphide-linked chains, alpha (residues 672–1663) and beta (residues 23–667), with removal of the signal sequence (residues 1–22).

(c) The mature protein contains a thiolester bond between residues Cys1010 and Gln1013.

(d) C3 convertases cleave C3 to remove C3a (residues 672–748). This reaction is followed by breakage of the thiolester bond.

(e) In the presence of factor H, factor I cleaves C3b between residues Arg1303 and Ser1304, and between Arg1320 and Ser1321.

Modifications made to the native C3 molecule
Replacement of Arg1303 by Gln

This modification is at one site of cleavage of C3b by factor I. The effect is to reduce the rate of cleavage by factor I at this position. The change to glutamine was selected to take away the positive charge of the arginine, which is likely to be important for the serine protease activity of factor I, while retaining a hydrophilic character and a similar side-chain size that should minimise any disruptions to the tertiary protein structure. Evidence supporting this presumption is that the mutation did not prevent processing into a two-chain structure, formation of a thiolester or cleavage of C3 by C3 convertase. Mutation of Arg1303 to another amino acid can achieve a similar or even a superior effect, as demonstrated in Example 5.

It may also be possible to reduce this cleavage by mutating Ser1304 (the other side of the cleavage site) or other residues involved in the enzyme-substrate interaction.
Replacement of Arg1320 by Gln This modification is at the other site of cleavage of C3b by factor I. The effect is to drastically reduce (virtually abolish) the rate of cleavage by factor I at this position. The change to glutamine was made on the same criteria described above, and this mutation also did not prevent processing into a two-chain structure, formation of a thiolester or cleavage of C3 by C3 convertase. Again, mutation to another amino acid may achieve the same effect, as may mutation of Ser1321 or other residues involved in the enzyme-substrate interaction.

When in combination the two mutations, Arg1303-Gln and Arg1320-Gln, protect the C3b from inactivation and hence maintain its ability to form part of an active C3bBb convertase. Other mutations (including combinations of mutations) that abolish both cleavage reactions could also be used (for example Arg 1303 Glu or Arg 1303 Gly could be used in combination with Arg 1320 Gln).

EXAMPLE 7

Various mutations that reduce the interaction of C3b/C3i with factor H 7.1 Introduction Other laboratories have produced evidence based either on the effects of synthetic peptides (Ganu, V. S. and Muller-Eberhard, H. J., 1985, *Complement* 2:27; Becherer, J. D. et al., 1992, *Biochemistry* 31: 1787–1794), or limited mutagenesis (Taniguchi-Sidle, A. and Isenman, D. E., 1994 *J. Immunol.* 153: 5285–5302) to suggest that the residues 752–761 in the primary sequence of the C3 transcript (see FIG. 1) could be involved in the interaction with factor H. However, other published evidence suggests that only residues 767–776 are involved in the interaction with factor H, whereas residues 752–761 are important for the interaction with factor B (Fishelson, 1991, Mol. Immunol. 28:545–552). We surmised that more extensive mutagenesis of this region might reduce the affinity for factor H and therefore be desirable for the objective of creating a C3 derivative that is resistant to factor H. Furthermore, we guessed that the important residues to mutate could be the prominent acidic residues (aspartic and glutamic acids) and that it would be desirable to change them to neutral residues less likely to mediate strong interactions. In this example we changed residue 752–754 from Asp-Glu-Asp to Gly-Ser-Gly, in combination with changing residues 758–760 from Glu-Glu-Asn to Gly-Ser-Gly. The product displayed reduced cleavage characteristics consistent with a reduction in the susceptibiliity to factor H. This provides evidence that C3 can be modified to reduce the binding of factor H, and hence the susceptibility to factors H and I. These modifications are desirable for the creation of a C3 convertase that is stable under physiological conditions.

7.2 Method

The methods of mutagenesis, expression and analysis have been described in the earlier examples. The mutagenic oligonucleotide that was synthesised had the sequence:

agtaacctgggttcgggcatcattgcaggatcgggcatcgtttcc.

7.3 Results

Figure 6:
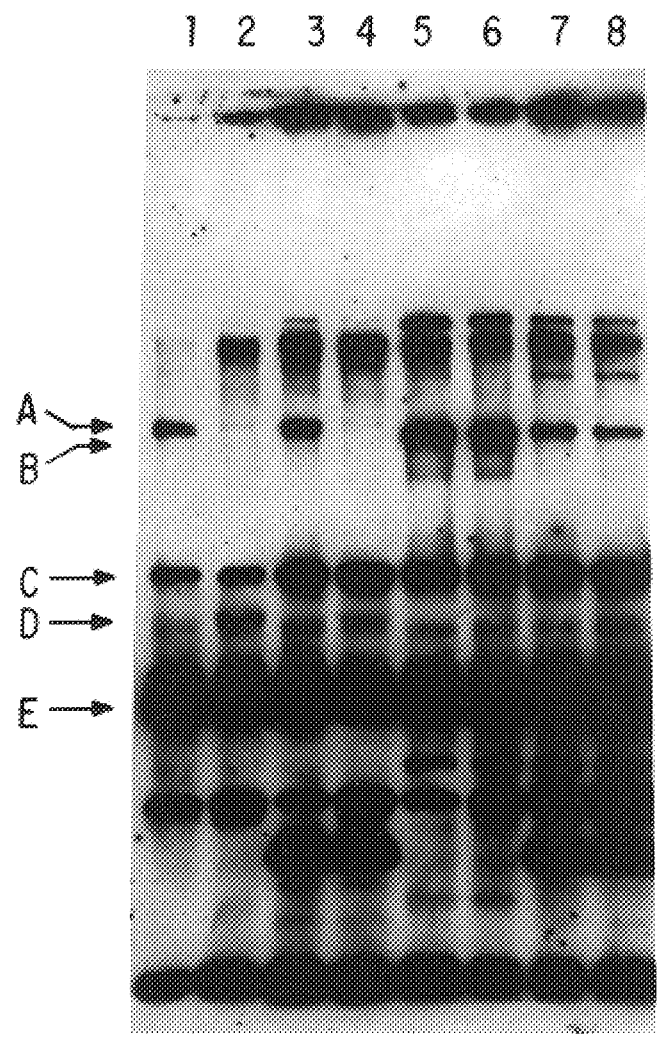
FIG. 6 shows an analysis of the cleavage of a C3 convertase mutated at amino acid residues 752–754 and 758–760.

The results of cleavage reactions are shown in FIG. 6. These indicate that:

1. Addition of CVFBb to wild-type C3 results in elimination of the alpha chain (track 2) because the C3b that is formed is susceptible to the low concentrations of factor I and H in the culture supernatant. C3i that has been formed during expression or this subsequent incubation has been broken down to iC3i in the same way. Addition of exogenous factors I and H (tracks 3 and 4) are therefore no different from tracks 1 and 2 respectively, because the medium itself contains sufficient factor H and I activity to effect complete cleavage.

2. In contrast, treatment of the mutant C3 with CVFBb (track 6) does not result in disappearance of the alpha chain. There is some generation of alpha', corresponding to C3b, but some or all of this remains, indicating that the persistence of alpha chain is not merely the result of a failure of cleavage by CVFBb. The remaining uncleaved alpha chain in track 2 may therefore represent C3i that has not been cleaved by the endogenous activities of factors H and I, although it is also possible that some of this represents native C3 persisting if the mutant has acquired a partial resistance to CVFBb. Addition of high concentrations of exogenous factors H and I (track 7 and 8) does produce depletion of alpha and alpha' chains, indicating that (i) the mutant is not completely resistant to these factors, and (ii) the alpha chain uncleaved by CVFBb in track 2 is predominantly derived from C3i (which is cleavable by factors H and I but not by CVFBb) rather than from native C3 (which is cleavable by CVFBb but not by factors H and I). Still not all the alpha chain is cleaved, even in track 8, probably because of the resistance to factors H and I.

Therefore mutation of residues 752–754, and residues 758–760 can generate a C3 molecule that can still be cleaved by C3 convertases, but is partially resistant to the actions of factors H and I. In view of other published data, this is most probably because the mutations have modified a region that is involved in the interaction with factor H and hence have resulted in a reduced affinity for factor H.

EXAMPLE 8

A site in C3 that can be mutated to modify the interaction of C3i with factor B 8.1 Introduction The previous examples have demonstrated that mutations to C3 can modulate the interactions with factors H and I. In order to discover other sites in C3 that might interact with factor B, we compared the known sequences of C3 molecules from different species, as well as with available sequences for C4 and other homologous proteins. We identified the region corresponding to residues 1427–1433 of human C3 that might be involved in C3 and C4 specific functions. This could include interaction with factor B (or its homologue, C2, in the case of C4), but not necessarily because other potential functions include thiolester formation, conversion into C3b (or C4b form), interaction with substrate C3 and/or C5 in convertase activity and interaction with factor I and its cofactors. Therefore selected residues were mutated to the corresponding residues (based on sequence alignments) found in another homologous protein, in this case human C5. Thus residue 1427 was changed from an Arg to a Gln, residue 1431 from a Lys to Asp, and residue 1433 from a Glu to a Gln. The resulting mutant was found to be susceptible to cleavage by C3 convertase (CVFBb) and the C3b product was cleavable by factors H and I. However, this mutant did not support the conversion of factor B to Bb plus Ba, which is dependent on the binding of factor B to C3i (or C3b). Therefore we have evidence that mutation of this region has diminished the interaction with factor B. Whilst this is undesirable for the generation of a super-active C3 convertase, it does provide an indication that other modifications to this region of C3 will also alter the interaction with factor B, and some of these will probably increase the affinity. As a consequence such mutations may also increase the stability and activity of the bimolecular convertase enzyme, C3bBb (or C3iBb).

8.2 Methods

The alignments shown in Table 1 overleaf illustrate why we considered hat this region was a candidate for mutagenesis. We surmised that characters of certain residues were well conserved in C3 and C4 but distinctly different in the other proteins. Residues 1427, 1431 and 1433 were selected because their charged nature might be indicative of groups involved in protein-protein interactions. The changes were made to the corresponding residues in human C5 because these displayed very different electrostatic properties, but within the context of some other conserved residues that might indicate a similar local structure.

TABLE 1

Alignments of sequences of C3 and related molecules for region of residues 1427–1435 of human C3

| Protein | Species | RESIDUE (Human) | | | | | | | | |
|---|---|---|---|---|---|---|---|---|---|---|
| | | 1427 | 1428 | 1429 | 1430 | 1431 | 1432 | 1433 | 1434 | 1435 |
| C3 | Human | R | Y | I | S | K | Y | E | L | D |
| | Mouse | R | Y | I | S | K | Y | E | M | N |
| | Rat | R | Y | I | S | K | Y | E | M | D |
| | G. pig | R | Y | I | S | K | Y | E | L | D |
| | Rabbit | R | Y | I | S | K | Y | E | L | N |
| | Cobra | R | Y | I | S | K | F | E | I | D |
| | Xenopus | K | Y | I | S | K | Y | E | V | N |
| | Trout | R | Y | I | E | K | F | E | M | D |
| C4 | Human | R | Y | V | S | H | F | E | T | E |
| | Mouse | R | Y | V | S | H | F | E | T | D |
| Slp | Mouse | R | Y | V | S | H | F | E | T | D |
| C3/C4-like | Hagfish | N | Y | I | V | Q | Y | E | I | R |
| | Lamprey | K | Y | I | S | N | Y | E | I | T |
| C5 | Human | Q | L | F | T | D | Y | Q | I | K |
| | Mouse | Q | L | L | T | D | Y | Q | I | K |
| A2M | Human | P | T | V | K | M | L | E | R | S |
| | Mouse | P | S | V | K | R | L | Q | D | Q |
| | Rat | P | T | V | K | M | L | E | R | S |
| PZP | Human | P | I | V | K | M | L | E | R | S |
| Murinoglobulin | Mouse | P | T | V | K | K | L | E | R | L |
| A1M | Rat | P | S | V | K | K | L | Q | D | Q |
| A1M | G. Hamster | P | T | V | K | K | L | E | R | S |
| A1I3 | Rat | P | T | V | K | K | L | E | R | L |

The methods of mutagenesis, expression and analysis of C3 cleavage reactions were as described in the earlier examples (Examples 1–4). The mutagenic oligonucleotide was synthesised with the sequence:

tggtgttgaccaatacatctccgactatcagctggacaa.

Assay for turnover of factor B.

The expressed product was purified from the COS cell medium by affinity purification on a column of Clone-3-Sepharose as described in Example 9. This method results in considerable conversion of the thiolester broken form, C3i. Wild-type C3 was isolated by the same procedure. Dilutions of the wild-type C3 (1/5, 1/25 and 1/125) were run on an SDS-PAGE gel (reducing conditions) along with the mutant C3, and silver staining indicated that the mutant was present at a concentration equivalent to slightly less than the 1/25 but much more than the 1/125 dilution of wild-type. The same dilutions were used in the assay of factor B turnover. 5 µl of these C3's were incubated with 25 µl of CFD-G containing 54 µg/ml factor D and approximately 1.6 µg/ml of $^{125}$I-labelled factor B (approx. 1000–2000 dpm/µl) for 3 h at 37° C. The samples were then analysed by SDS-PAGE (reducing conditions) with autoradiography of the dried gel. The results are shown in FIG. 7.

8.3 Results

As shown in FIG. 7, distinct cleavage of factor B occurs even at a 1/125 dilution of the wild-type C3 (C3i). In contrast, no significant cleavage was observed in the presence of the mutant C3, even undiluted which should be at a concentration higher than the 1/125 sample of the wild-type.

This mutant therefore appears to have an impaired ability to support the cleavage of factor B, most likely due to a reduction in its binding affinity for factor B. Therefore this is a region of C3 that can be mutated to modulate the interaction between C3i (or C3b) and factor B and perhaps also the stability of the convertase (C3iBb or C3bBb).

EXAMPLE 9

Purification of expressed mutant C3 molecules 9.1 Introduction

This example demonstrates how the mutant C3 molecules may be isolated from an expression medium, such as the culture medium of transfected eukaryotic cells. By simple affinity purification the C3 molecules are obtained in sufficient purity for functional tests and for conjugation to antibody by the method described in Example 10. Although elution from an antibody is accompanied by hydrolysis of a considerable proportion of the internal thiolester, the C3i product is still a suitable precursor for the generation of an active C3 convertase, as well as for the production of C3i-antibody conjugates. This approach is also likely to be useful as part of the preparation required for in vivo use.

9.2 Method

Affinity-purification on Clone-3-Sepharose. Clone-3 is a rat monoclonal antibody that is specific for C3 and its derivatives, including C3b and C3i (Lachmann, P. J. et al., 1980, J. Immunol. 41:503–515). Other monoclonal antibodies against C3 are available, and in some cases have been successfully used to isolate C3 from small quantities of human plasma (Dodds, A. W., 1993, Methods Enzymol. 223:46–61) and are therefore also likely to be applicable for the isolation of molecules expressed ex vivo. The IgG fraction was coupled to Sepharose CL-4B using cyanogen bromide (methodology may be found in Harrison and Lachmann, 1986, Handbook of Experimental Immunology, 4th edn., Ed.s Weir, Herzenberg, Blackwell and Herzenberg; Blackwell, Oxford). Culture supernatants were either passed directly through a column of this resin (re-circulated), or first concentrated by precipitation with 25% (w/v) $Na_2SO_4$, and resolubilization and dialysis into PBS, 5 mM $NaN_3$. The column is then washed successively with (i) PBS, 5 mM $NaN_3$ and (ii) PBS containing 1M NaCl. Bound C3 elutes with 50 mM Na borate buffer, pH 10.5, and is immediately neutralised by collection of 0.9 ml fractions into 0.1 ml 1M Tris/HCl pH 7. The material is then dialysed into PBS, 5 mM $NaN_3$.

Preparation of C3 bearing a "His-Tag"

A "His-Tag" is a string of histidine residues that displays affinity for columns bearing Nickel ions. This method has been employed to aid the isolation of expressed proteins. We thought that this could be useful for the isolation of expressed mutant C3 molecules so we have used insertion mutagenesis to generate a plasmid encoding C3 with a tail of 6 histidine residues at the carboxy terminus (immediately carboxy-terminal to residue 1663). This location for the his tag was selected so as to minimise interference with the synthesis, folding, processing and disulphide bond formation of the nascent C3. Residue 1661 is a cysteine residue that is involved in a disulphide bond to a residue earlier in the sequence (probably Cys 1537; Dolmer, K. and Sottrup-Jensen, L., 1993, *FEBS-Lett* 315: 85–90) and therefore it seemed prudent to make the insertion beyond this structural feature. The mutation was introduced using the "gapped-plasmid" technique used in Example 1, using the mutagenic oligonucleotide synthesised with the sequence:

tgggtgccccaaccatcatcatcatcatcattgaccacacccccc.

Incorporation of the correct sequence was confirmed by DNA sequencing. This DNA sequence may now be transferred to an expression vector. After transfection of eukaryotic cells, it should be possible to isolate the expressed C3 by affinity for a column bearing Nickel ions, or by any other matrix with specific affinity for the "His-Tag".

9.3 Results

A number of mutant C3 have been purified on the Clone-3-Sepharose, including those described in Examples 1 and 2 expressed in CHO cells. The products retained the ability to support the cleavage of factor B by factor D. The same method was used to isolate the mutant described in Example B2, expressed in COS cells. Silver-staining of SDS-PAGE gels indicated that the isolated products were not 100% pure, but often appeared to be greater than or equal to 50% pure. This comes from starting materials generally containing less than 10 $\mu$g/ml C3 in 10% (v/v) fetal calf serum plus other cellular proteins. In addition the C3's were not degraded during isolation, and endogenous factor H and I activity appeared to have been removed.

Purification by virtue of the "His-Tag" involves milder elution conditions from a column bearing Nickel ions. For example, EDTA has been used. Application of this method to C3 should therefore allow isolation without rupture of the internal thiolester bond.

EXAMPLE 10

Conjugation of C3i to antibody and use to target C3 convertase activity against a particular cell 10.1 Introduction One aspect of the invention is that stable C3 convertases derived from mutant C3 molecules will cause enhanced C3 conversion which, if localised at a particular target site, will promote complement-dependent attack of that target. The favoured approach for targeting the response is to couple the mutant C3 molecule, as either the C3i or C3b derivative, to an antibody specific for the desired target. In this example we demonstrate a working methodology for formation of such conjugates, which is applicable to mutant C3i or C3b molecules and can be used on material affinity-purified from an expression system, even if the thiolester of C3 has been broken in the process. By coupling C3i to an antibody that specifically binds to sheep erythrocytes, we further show that the the conjugate fixes C3i to the erythrocyte surface such that a convertase, C3iBbP, can be formed that initiates lysis of these cells when other complement components are supplied in the form of normal guinea-pig serum (in EDTA to prevent de-novo formation of C3 convertases). Hence conjugation to antibody can be used to target a C3i molecule to initiate complement-dependent attack of a particular cell type. This example uses wild-type C3i, from human plasma, that forma a C3 convertase in vitro. In vivo, wild-type C3i and C3b are broken down by factor H and I. Therefore a mutant C3, constructed according to the plans in this patent to be resistant to factors H and I and therefore forming a stable C3 convertase, would be advantageous in a physiological context.

10.2 Method (i) Generation and purification of C3i-antibody conjugate

The antibody used was the IgG fraction isolated from a polyclonal rabbit anti-sheep erythrocyte antiserum. 1.1 mg was incubated with 75 nmol of SPDP in conjugation buffer, pH 7.5 (20 mM $KH_2PO_4$, 60 mM $Na_2HPO_4$, 0.12M NaCl) for 2 h at room temperature. The PDP-IgG was purified by gel-filtration on a Superose-6 column (Pharmacia) (in a phosphate buffer, pH 7.4, containing 0.5M NaCl). Reduction of a sample with dithiothreitol was used to estimate 4 PDP groups coupled per molecule of IgG. C3i was prepared by treatment of purified C3 with 0.1M methylamine, pH 7.2 (2 h at 37° C.). Excess methylamine was removed by gel-filtration followed by dialysis into conjugation buffer. 18 nmole of C3i was mixed with 1.7 nmoles of PDP-IgG in 1.26 ml conjugation buffer and incubated for 1 day at room temperature followed by 1.5 days at 4° C. FIG. 8 shows a Coomassie Blue stained SDS-PAGE gel of the conjugation reaction mixture showing the appearance of a species of approximately 350 kDa that was not present in either PDP-IgG or C3i. This species was partially purified by gel-filtration on the Superose-6 column in a phosphate buffer, pH 7.4, containing 0.5M NaCl and then dialysed into PBS. It eluted before the C3, in a volume from which a molecular weight of 300–400 kDa could be estimated by calibration with globular molecular weight standards. Concentrations of conjugate, free antibody and uncoupled C3 were estimated from a Coomassie-stained SDS-PAGE gel (non-reducing conditions). Two-dimensional SDS-PAGE (first dimension unreduced, second dimension reduced) revealed a pattern compatible with a 1:1 conjugate between IgG and C3i.

(ii) Demonstration that the C3-antibody conjugate can be used to target convertase activity against a particular cell.

20 $\mu$l of dilutions of the conjugate (0 (no conjugate) 1/100, 1/50, 1/10) were incubated with 100 $\mu$of approximately 1% (v/v) sheep erythrocytes (prewashed in CFD) for 1 hour at 37° C. Parallel incubations were performed with equivalent amounts of PDP-IgG (no C3) and C3 alone. The cells were then washed 4 times in CFD and resuspended to 100 $\mu$l in CFD-G. 50 $\mu$l of this were lysed with 150 $\mu$l $H_2O$, followed by addition of 800 $\mu$l of CFD containing 10 mM EDTA and 2% (v/v) NGPS. The other 50 $\mu$l of conjugate-coated cells were incubated for 15 min at 37° C. with 50 $\mu$of CFD-G containing 190 $\mu$g/ml factor B, 2 $\mu$g/ml factor D, 20 $\mu$g/ml properdin and 0.6 mM $NiCl_2$, followed by lysis with 900 $\mu$of CFD containing 10 mM EDTA and 2% (v/v) NGPS. After 30 min at 37° C., the cells were pelleted by centrifugation (2000×g, about 3 min) and the optical absorbance of the supernatant was measured at 412 nm. Using the $H_2O$-treated samples as 100% lysis, and a buffer blank devoid of cells, the % lysis was calculated, as shown in FIG. 9. The conjugate produced dose-dependent lysis, whereas neither the PDP-IgG nor the C3i alone generated any lysis significantly above that observed in the absence of any such treatment.

10.3 Summary of Results

The method used has proved successful for coupling C3i to IgG as shown by:

1. The formation of a band of appropriate size (about 350 kDa) for a 1:1 C3:IgG conjugate shown by SDS-PAGE in FIG. 8.
2. Two-dimensional SDS-PAGE (first dimension non-reduced, second dimension reduced) indicated that this species contained both IgG and C3i.
3. The elution characteristic of this species on gel-filtration is again consistent with a molecule of about 350 kDa.
4. The conjugate displays a haemolytic activity that is not displayed by either PDP-IgG or C3i (FIG. 9).

The haemolytic assay (FIG. 9) further demonstrates that:

1. The specific anti-sheep erythrocyte antibody has localised the C3i to the target cell (sheep erythrocyte) membrane, preventing it from being removed by washing (in contrast to free C3i).
2. The conjugate retains the activity of the C3i in that it is still able to form a C3 convertase by reaction with properdin and factors B and D.
3. This convertase can initiate complement-dependent attack of the target, in this case by activating the lytic pathway (C5–9) to lyse the erythrocyte.

Additional data from other laboratories show that cobra venom factor can be coupled to an antibody and that these conjugates can target complement activation against a particular cell type (Vogel, 1988, *Targeted. Diagn. Ther.*, 1:191–224; Muller, B. and Muller-Ruchholtz, W., 1987, *Leuk. Res.* 11:461–468; Parker, C. J., White, V. F. and Falk, R. J., 1986, *Complement* 3:223–235; Petrella, E. C. et al, 1987, *J. Immunol. Methods* 104:159–172). These data support the contention that C3 modified so that it is capable of forming a stable C3 convertase, like cobra venom factor, could be used to target complement-mediated responses, as outlined in this invention.

EXAMPLE 11

Demonstration that mutant C3 molecules induce factor B turnover in normal human serum 11.1 Introduction A major purpose of the invention described herein is the consumptive depletion of complement activity from biological fluids. The invention describes methods for the manufacture of C3 molecules that are resistant to down-regulation by factors H and I. In this state they will bind factor B and generate active C3 convertases. The activity of these convertases is demonstrated by the haemolytic assay employed in Example 6. Such a convertase will therefore consume C3. If the convertase is unstable, it will dissociate without much C3 conversion. However this will allow binding of fresh factor B, and its conversion to Bb and Ba. Thus the mutant C3 will promote the consumption of factor B, leading ultimately to the disablement of the alternative pathway, and its inability to amplify classical pathway stimulation. If a stable C3 convertase is formed, turnover of factor B will be reduced, but consumption of C3 will be increased. Both situations can therefore be desirable. In this example we demonstrate that mutant C3 molecules that are modified to make them resistant to factor I, but without any modification to modify the stability of the convertase, promote accelerated turnover of factor B in human serum. Wild-type C3, in contrast, causes no significant turn-over, presumably because wild-type C3i is rapidly degraded by factors H and I.

11.2 Method

The Mutants prepared are as follows:

Q1R2 Arg1303 changed to Gln (Example 2)

Q1Q2 Arg1303 changed to Gln, plus Arg1320 changed to Gln (Example 1)

E1Q2 Arg1303 changed to Glu, plus Arg1320 changed to Gln (Example 5)

These mutants were all expressed in CHO cells and then purified by precipitation with $Na_2SO_4$, followed by affinity purification on Clone-3-Sepharose, as described in Example B3. Wild-type C3 (R1R2) was similarly isolated. By SDS-PAGE with silver-staining, the concentration of Q1 was between 1/5 and 1/25 of the wild-type, the concentration of Q1Q2 was about that of 1/5 wild-type, and the concentration of E1Q2 was between 1/25 and 1/125 of wild-type. All preparations probably contained a majority of thiolester-broken molecules (C3i).

10 $\mu$l of these C3 preparations were incubated with 10 $\mu$l of a solution of 20% (v/v) normal human serum in PBS containing 1 mM $MgCl_2$ and approximately 300 ng $^{125}$I-labelled factor B (approx. 2–300,000 dpm) for 1 hour at 37° C. 5 $\mu$l was then analysed by SDS-PAGE (reducing conditions). The dried gel was exposed to autoradiography film to indicate the positions of the bands corresponding to the intact factor B and its cleavage products. These were then excised and counted to accurately determine the degree of cleavage. The value obtained in buffer alone was subtracted as background (encompassing not only background cleavage, but also degradation products and other impurities present in the radioligand preparation.

11.3 Results

The resulting degrees of factor B cleavage are shown below:

| | |
|---|---|
| 1/25 Wild-type | 1.49% |
| 1/5 Wild-type | 2.74% |
| Q1R2 | 6.19% |
| Q1Q2 | 7.41% |
| E1Q2 | 6.42% |

Therefore the factor I resistant mutants all produce greater levels of factor B cleavage than equivalent amounts of wild-type C3 (C3i). With larger doses or longer incubations, complete incapacitation of the alternative pathway should result.

The abbreviations used in the foregoing examples include: CFD, complement fixation diluent (defined in Harrison and Lachmann, 1986, *Handbook of Experimental Immunology*, 4th edn., Ed.s Weir, Herzenberg, Blackwell and Herzenberg; Blackwell, Oxford); CFD-G, CFD containing 0.1% (w/v) gelatin; PBS, phosphate-buffered saline; NGPS, normal guinea-pig serum; SDS-PAGE, SDS-polyacrylamide gel electrophoresis; SPDP, N-Succinimidyl-3-[2-pyridyldithio]propionate.

REFERENCES:

1. Bergmann, M. & Fruton, J. S. (1941) *Adv. Enzymol.*, 1:63–98.
2. de Bruijn, M. H. & Fey, G. H. (1985), *Proc. Natl. Acad. Sci. U.S.A.* 82:708–712
3. Crawford-M H et al. (1988) *Circulation.* 78:1449–58
4. Daha, M. R. & van Es, L. A. (1982) *Immunol.* 43:33–38.
5. Farries, T C; Lachmann, P J & Harrison, R A (1988) *Biochem. J.* 252:47–54
6. Farries, T C; Lachmann, P J & Harrison, R A (1988) *Biochem. J.* 253:667–75
7. Forty, J; Hasan, R; Cary, N; White, D J & Wallwork, J (1992) *Transplant. Proc.* 24:488–9

8. Fritzinger, D. C. et al. (1992) *J. Immunol.* 149:3554–3562
9. Harrison, R. A. & Lachmann, P. J. (1980) *Mol. Immunol.* 17:9–20.
10. Kalli, K. R., Hsu, P. & Fearon, D. T. (1994) *Springer Semin. Immunopathol.* 15:417–431.
11. Kinoshita, T; Takata, Y; Kozono, H; Takeda, J; Hong, K S & Inoue, K (1988) *J. Immunol.* 141:3895–901
12. McNearney, T A; Odell, C; Holers, VM; Spear, PG; Atkinson, J P (1987) *J. Exp. Med.* 166:1525–35
13. Nicol, P. A. E. & Lachmann, P. J. (1973) *Immunol.* 24:259–275
14. Pangburn, M K & Muller-Eberhard, H J (1984) *Springer Semin. Immunopathol.* 7:163–92
15. Rother, K. & Till, G. O. (eds) (1988) *"The complement System"* (Springer-Verlag Berlin Heidelberg, Germany)
16. Van den Berg, C. W., Aerts, P. C. & Van Dijk, H. (1991) *J. Immunol. Methods* 136:287–294.
17. Vogel, C W; Smith, C A & Muller-Eberhard, H J (1984) *J. Immunol.* 133:3235–41
18. Weisman, H F et al. (1990) *Science* 249:146–51.
19. Wu, R. (ed.) (1993) *Methods Enzymol.* 217: ch.s 12–14 (Academic Press, San Diego, U.S.A.)
20. Botto, M, Fong, K. Y., So, A. K., Koch, C. & Walport, M. J. (1990) *J. Exp. Med.* 172:1011–7
21. Sambrook, J., Fritsch, E. F. & Maniatis, T. (1989) *"Molecular Cloning. A Laboratory Manual,"* second edition (Cold Spring Harbor Laboratory Press)
22. Fishelson, Z. (1991) *Mol. Immunol.* 28:545–52.
23. Taniguchi-Sidle, A & Isenman, D. E. (1993) *Mol. Immunol.* 30:54.
24. Lambris, J. D., Avila, D., Becherer, J. D. & Muller, Eberhard, H. J. (1988) *J. Biol. Chem.* 263:12147–50.
25. Taniguchi-Sidle, A. and Isenman, D. E. (1992) *J. Biol. Chem.* 267:635–643.
26. Hofer, B. and Kuhlein, B. (1993) *Methods Enzymol.* 217:173–189.
27. Morinaga, Y., Franceschini, T., Inouye, S. and Inouye, M. (1984) *Bio-technology* 2:636–639.
28. Harrison, R. A. and Lachmann, P. J. (1986) *"Handbook of Experimental Immunology"* (eds Weir, Herzenberg, Blackwell and Herzenberg;Blackwell, Oxford) 4th ed.,
29. Kotwal, G., J., and Moss, B., *Nature* (1988) 335 (6186) :176–8.

---

We claim:

1. A modified human C3 protein which is capable of forming a stable C3 convertase wherein said modified protein is selected from the group consisting of:
   (a) a C3 protein in which either Arg-1303, Arg-1320, or both is replaced with another amino acid;
   (b) a C3 protein which has reduced susceptibility to Factor H and/or Factor I relative to native human C3 convertase, said protein having one or more amino acid changes relative to native human C3 convertase in the region corresponding to amino acid residues 752–754 and/or residues 758–780 of native human C3 convertase; and
   (c) a C3 protein having amino acid changes relative to native human C3 convertase at amino acid residues 1427, 1431 and/or 1433 of native human C3 convertase.

2. A protein as claimed in claim 1 wherein the protein is modified by replacement of either Arg-1303, Arg-1320, or both by another amino acid.

3. A protein as claimed in claim 2 wherein Arg-1303, Arg-1320 or both are replaced by glutamine, tyrosine, cysteine, tryptophan, glutamic acid or glycine.

4. A protein as claimed in claim 3, wherein Arg-1320 is replaced by glutamine.

5. A protein as claimed in claim 3 wherein Arg-1303 is replaced by glutamic acid, glycine or glutamine.

6. A protein according to claim 1 which has reduced susceptibility to Factor H and/or Factor I relative to native human C3 convertase, said protein having one or more amino acid changes relative to native human C3 convertase in the region corresponding to amino residues 752–754 and/or residues 758–780 of native human C3 convertase.

7. A protein according to claim 6 wherein the one or more amino acid changes are changes from acidic amino acid residues to neutral amino acid residues.

8. A protein according to claim 7 wherein the amino acid residue changes are changes from Asp-Glu-Asp to Gly-Ser-Gly.

9. A protein according to claim 1 having amino acid changes relative to native human C3 convertase at amino acid residues corresponding to residues 1427, 1431 and/or 1433 of native human C3 convertase.

10. A conjugate comprising a protein as defined in claim 4 linked to a specific binding moiety.

11. A conjugate as claimed in claim 10 wherein the specific binding moiety is a specific binding protein.

12. A conjugate as claimed in claim 11 wherein the specific binding protein is an antibody or antigen binding fragment thereof.

13. A pharmaceutical formulation comprising a modified human C3 protein as defined in claim 1 or a conjugate as defined in claim 10 together with one or more pharmaceutically acceptable carriers or excipients.

14. A method of reducing complement pathway protein in a mammal which comprises administering to the mammal a protein as defined in claim 4.

15. A method of reducing complement pathway protein in a mammal which comprises administering to the mammal a pharmaceutical formulation as defined in claim 13.

* * * * *